(12) United States Patent
Anderson et al.

(10) Patent No.: US 11,172,987 B2
(45) Date of Patent: *Nov. 16, 2021

(54) METHOD AND APPARATUS FOR SELECTIVE TREATMENT OF BIOLOGICAL TISSUE

(71) Applicants: The General Hospital Corporation, Boston, MA (US); Blossom Innovations, LLC, Waltham, MA (US)

(72) Inventors: Richard Rox Anderson, Boston, MA (US); Dieter Manstein, Coral Gables, FL (US); Henry Hin Lee Chan, Hong Kong (CN); Vincent Zuo, Boston, MA (US)

(73) Assignees: The General Hospital Corporation, Boston, MA (US); Blossom Innovations, LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/227,918

(22) Filed: Apr. 12, 2021

(65) Prior Publication Data

US 2021/0298828 A1 Sep. 30, 2021

Related U.S. Application Data

(63) Continuation of application No. 15/853,318, filed on Dec. 22, 2017, now Pat. No. 10,973,578.

(Continued)

(51) Int. Cl.
*A61B 18/20* (2006.01)
*A61B 18/00* (2006.01)

(52) U.S. Cl.
CPC .. *A61B 18/203* (2013.01); *A61B 2018/00452* (2013.01); *A61B 2018/00577* (2013.01);

(Continued)

(58) Field of Classification Search
CPC ............ A61B 18/203; A61B 18/20553; A61B 2018/20355; A61B 2018/00452;
(Continued)

(56) References Cited

U.S. PATENT DOCUMENTS 6,997,923 B2 2/2006 Anderson et al.
8,221,400 B2 7/2012 Lubatschowski et al.
(Continued)

FOREIGN PATENT DOCUMENTS

JP 2010507412 A 3/2010
KR 1020160042069 A 4/2016
(Continued)

OTHER PUBLICATIONS

M. Rajadhyaksha, In vivo confocal scanning laser microscopy of human skin: melanin provides strong contrast, J Invest. Demol., 104(6), 946-52, Jun. 1995.

(Continued)

*Primary Examiner* — Jonathan T Kuo
(74) *Attorney, Agent, or Firm* — Hunton Andrews Kurth LLP

(57) ABSTRACT

An exemplary treatment system can be provided which can include a laser system configured to emit at least one laser beam, and an optical system configured to focus the laser beam(s) to a focal region at a selected distance from a surface of a tissue. The focal region can be configured to illuminate at least a portion of a target. The optical system can cause an irradiation energy transferred to the focal region of the laser beam(s) to (i) generate a plasma in a first region of the tissue adjacent to the target, and (ii) avoid a generation of a plasma in a second region of the tissue. The optical system has a numerical aperture that is in the range of about 0.5 to about 0.9. An exemplary method can also be provided to control such treatment system.

23 Claims, 14 Drawing Sheets

Related U.S. Application Data

(60) Provisional application No. 62/438,818, filed on Dec. 23, 2016.

(52) U.S. Cl.
CPC ............... *A61B 2018/00625* (2013.01); *A61B 2018/00642* (2013.01); *A61B 2018/00696* (2013.01); *A61B 2018/00708* (2013.01); *A61B 2018/20355* (2017.05); *A61B 2018/20553* (2017.05)

(58) Field of Classification Search
CPC ........... A61B 2018/00577; A61B 2018/00625; A61B 2018/00642; A61B 2018/00696; A61B 2018/00708; A61B 18/20–18/28; A61N 5/06–2005/073
See application file for complete search history.

(56) References Cited

U.S. PATENT DOCUMENTS

| | | | |
|---|---|---|---|
| 8,562,595 B2 | 10/2013 | Plunkett et al. | |
| 8,821,482 B2 * | 9/2014 | Verhagen | A61B 5/1077 606/9 |
| 2003/0216719 A1 | 11/2003 | Debenedictis et al. | |
| 2007/0055221 A1 | 3/2007 | Lubatschowski et al. | |
| 2007/0159592 A1 | 7/2007 | Rylander et al. | |
| 2010/0063490 A1 * | 3/2010 | Verhagen | A61B 5/1077 606/9 |
| 2011/0306919 A1 | 12/2011 | Latina et al. | |
| 2012/0010603 A1 | 1/2012 | Milner et al. | |
| 2014/0288539 A1 | 9/2014 | Bischoff et al. | |
| 2016/0199132 A1 | 7/2016 | Anderson et al. | |
| 2018/0177550 A1 | 6/2018 | Anderson et al. | |

FOREIGN PATENT DOCUMENTS

| | | |
|---|---|---|
| WO | 2008001284 A1 | 1/2008 |
| WO | 2015021462 | 2/2016 |
| WO | 2018119453 | 3/2021 |

OTHER PUBLICATIONS

International Search Report and Written Opinion dated Feb. 16, 2018 for International Application No. PCT/US2017/068330.

Lee, Ho, Yeon-Uk Jeong, and Kin F. Chan. "The advent of laser therapies in dermatology and urology: Underlying nechanisms, recent trends and future directions." Journal of the Optical Society of Korea 13.3 (2009): 321-329. (Year 2009).

American Society for Laser Medicine and Surgery Abstracts, 2016; https://onlinelibrary.wiley.com/doi/pdf/10.1002/sm.22485 (Year: 2016).

Anderson et al., "Selective Photothermolysis: Precise Microsurgery by Selective Absorption of Pulsed Radiation," Science, vol. 220, No. 4596, pp. 524-527, 1983.

European Search Report dated Jun. 26, 2020 for European Patent Application No. 17883882.7.

Canadian Examination Report dated Mar. 28, 2021 for Canadian Patent Application No. 3,047,587.

Lee, Ho, Yeon-Uk Jeong, and Kin F. Chan. "The advent of laser therapies in dermatology and urology: Underlying mechanisms, recent trends and future directions." Journal of the Optical Society of Korea 13.3 (2009): 321-329. (Year 2009).

American Society for Laser Medicine and Surgery Abstracts, 2016; https://onlinelibrary.wiley.com/doi/pdf/10.1002/lsm.22485 (Year: 2016).

Anderson et al., "Selective Photothennolysis: Precise Microsurgery by Selective Absorption of Pulsed Radiation," Science, vol. 220, No. 4596, pp. 524-527, 1983.

\* cited by examiner 710  712  714

716  718  720

METHOD AND APPARATUS FOR SELECTIVE TREATMENT OF BIOLOGICAL TISSUE

CROSS-REFERENCE TO RELATED APPLICATION(S)

This application is a continuation of U.S. Non Provisional patent application Ser. No. 15/853,318 filed Dec. 22, 2017, which issues as U.S. Pat. No. 10,973,578 on Apr. 13, 2021, which relates to and claims priority from U.S. Provisional Patent Application Ser. No. 62/438,818 filed on Dec. 23, 2016, the entire disclosures of which are incorporated herein by reference in its entirety.

FIELD OF THE DISCLOSURE

Exemplary embodiments of the present disclosure relates to affecting pigmented biological tissue, and more particularly to methods and apparatus for selectively generating local plasma effects in pigmented regions of such tissue.

BACKGROUND INFORMATION

Affecting biological tissue with optical (light) energy has gained widespread use over the past few decades. Optical energy is a form of electromagnetic energy. In the electromagnetic spectrum, optical energy can typically range from the infrared regime (longer wavelengths) to the ultraviolet regime (shorter wavelengths). Treatment of biological tissue with optical energy typically involves introducing the optical energy into the tissue.

When optical energy is directed onto or into biological tissue, there are three primary interactions that can occur. First, some portion of the energy may be reflected from the surface of the tissue. Such reflection may be wavelength-dependent, and the fraction of reflected energy can be reduced, e.g., by appropriate selection of energy wavelength, reducing variations in refractive index in the optical path (e.g., by using certain waveguide materials, providing a material coatings such as a gel on the tissue surface, etc.), and by selecting an appropriate angle of incidence of the beam on the tissue surface.

Optical energy can also be scattered by components in the tissue, which leads to local changes in direction of a portion of the optical beam energy. In some instances, scattering near the tissue surface can lead to a portion of the optical energy being scattered back out of the tissue surface (remission). If a tissue is relatively thin, some of the optical energy may pass through the tissue and exit it, usually after some scattering has occurred.

The primary mechanism of interest for affecting tissue is absorption. Energy absorbed by tissue components can produce several effects. For example, energy absorption can lead to generation/enhancement of vibrational modes of molecules and local heating effects. Local absorption of high-intensity optical energy (generally over short timeframes) can even produce vaporization (or ablation) of tissue, where local tissue components are broken down and converted to a gaseous state. Such photo ablation can produce rapidly-expanding small vapor bubbles in the tissue, which can generate mechanical (as well as thermal) disruption of nearby tissue, or ejection of tissue fragments from the tissue surface. Optical energy absorption can also lead to electron transitions, where electrons in an atom or molecule can be excited to a higher (quantized) energy state. These absorption mechanisms are linear, in which the absorption is substantially independent of the intensity of the optical energy. The relative extent and efficiency of the absorption processes depend on many factors, including the nature of the absorbing material/component, the wavelength(s) of the optical energy, etc.

The three classes of optical energy sources typically used to affect biological tissue are: 1) low power light sources such as lamps and light-emitting diodes; 2) intense pulsed light (IPL) sources; and 3) lasers. IPL sources, such as flashlamps, generally provide high-intensity pulses of non-collimated light beams having a range or spectrum of electromagnetic energy wavelengths. In contrast, lasers produce intense collimated beams of energy that are composed of one or more discrete wavelengths of coherent (in-phase) light. Lasers are preferred for many types of optical treatments because the effects of the optical energy can be better controlled when tissue is irradiated with a known wavelength of light.

Lasers can provide optical energy as a continuous wave (CW), with a continuous beam of energy, or as a series or sequence of energy pulses. Pulsed lasers can be generated by so-called Q-switching, mode locking, or in some cases by mechanical or electro-optical shuttering. Pulsed lasers are known in the art, and can be constructed to provide many combinations of wavelength, pulse duration, and pulse intervals, as well as different amounts of energy per pulse. Laser beams can also be shaped using various waveguides and/or lenses, etc., to produce energy beams having various beam shapes, widths, and focal characteristics. Accordingly, certain lasers and their operating parameters can be tailored to produce a broad range of effects in biological tissues.

It has been observed that application of light or optical energy of certain wavelengths can be strongly absorbed by chromophores, which are certain molecules or portions thereof that are particularly efficient absorbers of certain wavelengths of light. Chromophores can also govern the apparent color or appearance of certain tissue regions. Chromophores in biological tissue are often located in certain pigmented cells or structures, such as melanosomes or hair follicles. One common chromophore in skin tissue is melanin, which determines the general skin color of people. Hemoglobin in blood is another common biological chromophore. Chromophores in tissue can also be introduced from an external material, such as the light-absorbing nanoparticles of skin tattoos or some topically-applied compounds. Other chromophores that may be present in biological tissue can include, e.g., tattoo inks, sebaceous glands, subcutaneous fat, hair bulbs, lipids in cell membranes, fat surrounding organs, blood vessels, and drug components.

A key concept in affecting biological tissue with optical energy is selective photothermolysis, where characteristics of optical energy used to irradiate biological tissue are selected to provide preferential absorption of such energy by certain chromophores, with relatively little energy being absorbed by other regions of tissue that do not contain the chromophore(s). Selective or preferential absorption of the optical energy by chromophores can lead to local heating of the adjacent tissues, which can lead to thermal damage or necrosis of cells, physical changes in the heated tissue (e.g. coagulation, denaturation of collagen, etc.), and even vaporization of tissue.

Another factor affecting light/tissue interactions is the local thermal relaxation time. For example, in selective photothermolysis, the thermal heating and tissue damage can be localized to chromophore-containing regions if the duration of local irradiation is relatively short compared to the local thermal relaxation time, which is a characteristic time in which a small source of heat will diffuse into the surrounding tissue. In contrast, longer local irradiation times can lead to more widespread thermal damage arising from diffusion of heat away from the preferential absorption site. General principles of selective photothermolysis are described, e.g., in R. R. Anderson et al., Selective Photothermolysis: Precise Microsurgery by Selective Absorption of Pulsed Radiation, *Science*, Vol. 220, No. 4596. pp. 524-527 (1983).

Irradiation of biological tissue with high-intensity optical energy can vaporize or ablate tissue, as noted previously. Certain ablative lasers can be used, e.g., to effectively cut tissue using light energy, and are common in many ophthalmic procedures such as corneal refractive surgery. For example, precise ablation of corneal tissue can be achieved using nanosecond pulses of an ArF excimer laser, which emits light at a wavelength of 193 nm. The very short pulse durations minimize thermal damage away from the focused zones of direct irradiation.

Irradiation of tissue with high-intensity optical energy beams can also lead to dielectric breakdown of tissue components and formation of a plasma. For example, focused laser pulses with very short durations (e.g., on the order of a few nanoseconds or less, often pico-second or femto-second pulse durations) and very high power densities (e.g., $10^{10}$ W/cm$^2$ or more) can produce an electric field strength that is high enough to tear electrons away from atoms. At very high local power densities, a plasma may be formed in the tissue, in which free electrons absorb even more energy and collide with other atoms and molecules, ejecting more electrons (ionization) that also absorb energy from the optical energy beam. This can produce a chain reaction that results in a plasma formation, which is often accompanied by rapid local expansion and mechanical shockwaves in the tissue. These effects can be used to generate certain types of damage and vaporization of the tissue. Plasma formation is an example of a non-linear process that depends on the presence of a high optical power density, and does not occur at the low optical power densities (expressed in units, e.g., of W/cm$^2$) typical of lamps, IPLs, and continuous wave lasers. A pulsed laser source, typically focused to achieve sufficiently high power density over very short time intervals, is used. Once a plasma is formed, the free electrons and ions within the plasma absorb incoming light, which sustains the plasma until the end of the laser pulse.

There are many known uses for plasma formation in materials. For example, pulsed laser etching within glass or other transparent materials is an industrial example of a plasma formed by dielectric breakdown. In the medical field, posterior capsule cutting by a focused Q-switched laser after cataract removal is an example of using dielectric breakdown to generate a plasma that can locally vaporize tissue. More generally, dielectric breakdown at the focal spot of a Q-switched nanosecond or picosecond laser, which depends on power density, is commonly used in ophthalmology to cut structures within the eye by locally scanning or moving the laser focal point within the structure desired to be cut.

Plasma formation in tissue is often accompanied by a visible spark or flash of light and audible sound. Further absorption of the optical energy becomes non-linear in the plasma, where the absorption scales as the fourth power of the beam intensity. The heated electrons and ions can have extremely high temperatures on the order of $10^5$ K and local pressures on the order of kilobars. Because of the very high power densities and mechanisms of optical (or dielectric) breakdown, formation of plasma in tissue tends to be nonselective with respect to the presence of chromophores.

Therefore, it may be desirable to provide method and apparatus that can selectively produce plasmas and associated damage mechanisms in biological tissue, without generating excessive damage to non-targeted tissue or producing other undesirable side effects.

SUMMARY OF EXEMPLARY EMBODIMENTS OF THE DISCLOSURE

Exemplary embodiments of methods and apparatus can be provided for a treatment of biological tissue, for example, to selectively generate local plasma effects in pigmented regions of such tissue. The exemplary embodiments of the methods and apparatus can facilitate a selective energy absorption by pigmented or chromophore-containing structures and/or regions within biological tissues (e.g., skin tissue) by focusing highly-convergent electromagnetic radiation (EMR), e.g., optical energy, having appropriate wavelengths and other parameters onto regions within the tissue. This exemplary procedure can produce a sufficient selective absorption of local energy densities in the tissue to result in a production of plasmas in the biological tissue, e.g., arising from thermionic plasma initiation, which are selective to chromophore-containing tissue regions. Such localized plasmas can disrupt the pigment and/or chromophores while avoiding unwanted damage to surrounding unpigmented tissue and the overlying tissue. Such systems and methods described herein can be used, e.g., to improve appearance of skin tissue.

According to certain exemplary embodiments of the present disclosure, an apparatus can be provided that can include a radiation emitter arrangement configured to emit EMR, and an optical arrangement configured to direct the EMR onto the skin being treated and focus it to a focal region within the tissue. The EMR can be optical energy preferably having wavelengths in the near-infrared, visible, and/or ultraviolet portions of the electromagnetic energy spectrum. The source of the EMR can be or include, e.g., a laser system or the like. The apparatus can further include a housing and/or handpiece that can contain these components and facilitate manipulation of the apparatus during its use.

The EMR emitter can include, e.g., an EMR source such as one or more diode lasers, a fiber laser, or the like, and optionally a waveguide or optical fiber configured to direct EMR from an external source. If the emitter arrangement includes a source of EMR, it can optionally also include a cooling arrangement configured to cool the EMR source(s) and prevent overheating of the source(s). A control arrangement can be provided to control the operation of the emitter arrangement including, e.g., turning the EMR source on and off, controlling or varying parameters of the EMR source such as average or peak power output, pulse length and duration, etc.

The EMR can have a wavelengths that is preferably greater than about 600 nm, e.g., between about 600 nm and about 1100 nm. The selection of a particular wavelength can be based on the absorption spectrum of one or more particular chromophores. Wavelengths outside of this exemplary range can be used in certain exemplary embodiments, depending on the chromophores present, focusing properties of the optical energy beam(s), and/or parameters of the energy beam(s). For example, shorter wavelengths (e.g., less than about 600 nm) can be scattered significantly within the skin tissue, and may lack sufficient penetration depth to reach portions of the dermal layer with sufficient fluence and focus, but a high absorption coefficient for a particular chromophore may offset some of these effects.

The exemplary apparatus can include an optical arrangement configured to focus the EMR in a highly convergent beam. For example, the optical arrangement can include a focusing or converging lens arrangement having a numerical aperture (NA) of about 0.5 or greater, e.g., between about 0.5 and 0.9. The correspondingly large convergence angle of the EMR can provide a high fluence and intensity in the focal region of the lens with a lower fluence in the overlying tissue above the focal region. Such focal geometry can help reduce unwanted thermal damage in the overlying tissue above the targeted tissue regions. The exemplary optical arrangement can further include a collimating lens arrangement configured to direct EMR from the emitting arrangement onto the focusing lens arrangement.

The exemplary apparatus can be configured to focus the EMR such that a local intensity or power density of the optical energy in the focal region is about $10^{10}$ W/cm$^2$ or more, for example, between about $10^{10}$ W/cm$^2$ and $10^{11}$ W/cm$^2$ for optical energy having a wavelength of about 1060 nm. In certain embodiments, the local power density can be lower, e.g., as low as about $10^{8}$ W/cm$^2$, if other parameters such as absorption efficiency (which depends in part on the chromophore and on wavelength of the optical energy) and energy density (which also depends in part on pulse duration) are selected appropriately. An optical arrangement can be provided to focus the EMR to a small spot size in the focal region, e.g., a spot size (as measured in air with reduced scattering) between about 5 μm and about 100 μm. Such small focal spot sizes can facilitate generation of sufficiently high local power densities in the foal region. Somewhat smaller or larger spot sizes can be used in certain exemplary embodiments, e.g., depending on other factors such as wavelength(s) of the optical energy and absorption coefficient by a particular chromophore at such wavelength(s).

The exemplary optical arrangement can also be configured to direct the focal region of the EMR onto a location within the biological tissue (e.g., skin tissue or the like) that is at a depth below the surface of between about 5 μm and 2000 μm (2 mm), e.g., between about 5 μm and 1000 μm. This focal depth can correspond to a distance from a lower surface of the apparatus configured to contact the tissue surface and the location of the focal region. In further embodiments, the optical arrangement can be configured to vary the depth of the focal region and/or to provide a plurality of focal regions having different depths simultaneously.

In further exemplary embodiments of the present disclosure, the positions and/or orientations of the EMR emitter arrangement and/or components of the optical arrangement can be controllable and/or adjustable relative to one another and/or relative to the tissue, such that the location and/or path of the focal region(s) in the tissue can be varied. Such variation in the path of the focal region(s) can be provided using optical arrangements having variable focal lengths, mechanical translators that can controllably vary the position of the optical arrangement and/or EMR emitter arrangement relative to the tissue being treated, etc. Such exemplary variations in location of the focal region(s) can facilitate treatment of larger volumes of the tissue by "scanning" the focal region(s) within the tissue, e.g., in a pattern at a particular depth and/or at multiple depths. In certain exemplary embodiments, a mechanical translator can be provided having scan speeds over an area of tissue to be treated that range from, e.g., about 5 mm/sec to about 5 cm/sec.

In further exemplary embodiments of the present disclosure, a handpiece can be provided that is configured to be manually translated over the tissue at similar speeds. Sensor arrangements can be provided in such manual handpieces or in mechanically-translated devices to detect scanning speeds and affect parameters of the EMR source (such as EMR pulse duration, pulse frequency, pulse energy, etc.) and/or optical arrangement based on such detection, e.g., to maintain a consistent range of parameters such as local power density and local dwell times during treatment. For example, scanning speeds and focal region spot sizes can be selected to maintain a sufficiently small local dwell time of the focal region at a location in the tissue (e.g. less than about 1-2 ms) to avoid damaging unpigmented tissue.

In still further exemplary embodiments of the present disclosure, the exemplary optical arrangements can include a plurality of micro-lenses, e.g., convex lenses, plano-convex lenses, or the like. Each of the micro-lenses can have a large NA (e.g., between about 0.5 and 0.9). The micro-lenses can be provided in an array, e.g., a square or hexagonal array, to produce a plurality of focal regions in the dermal tissue in a similar pattern. A width of the micro-lenses can be small, e.g., between about 1 mm and 3 mm wide. Micro-lenses that are slightly wider or narrower than this can also be provided in certain embodiments. In yet further exemplary embodiments of the present disclosure, the micro-lenses can include cylindrical lenses, for example, convex cylindrical lenses or plano-convex cylindrical lenses. A width of such cylindrical micro-lenses can be small, e.g., between about 1 mm and 3 mm wide. A length of the cylindrical micro-lenses can be between, e.g., about 5 mm and 5 cm. Other exemplary arrangements of a plurality of small lenses can be used in further exemplary embodiments to generate a plurality of focal regions within the tissue, where such focal regions may be provided at the same or different depths (e.g., one or more micro-lenses may have a different focal length than another micro-lens).

The exemplary radiation emitter arrangement and/or the exemplary optical arrangement can be configured to direct a single wide beam of EMR over the entire array of such micro-lenses or a portion thereof to simultaneously generate a plurality of focal regions in the dermis. In further exemplary embodiments of the present disclosure, the radiation emitter arrangement and/or the optical arrangement can be configured to direct a plurality of smaller beams of EMR onto individual ones of the micro-lenses. Such multiple beams can be provided, e.g., by using a plurality of EMR sources (such as laser diodes), a beam splitter, or a plurality of waveguides, or by scanning a single beam over the individual micro-lenses. If cylindrical micro-lenses are provided, one or more beams of EMR can be scanned over such cylindrical lenses, e.g., in a direction parallel to the longitudinal axis of such cylindrical lenses.

In yet another exemplary embodiment of the present disclosure, a laser pulse having a relatively short duration on the order of, e.g., 10 μs, could be used to selectively heat the pigmented cells to liberate some electrons via thermionic emission. A second optical energy pulse having appropriate parameters, as described herein, including a pulse duration on the order of approximately 100 ns, can then be focused to irradiate the same pigmented cells and "pump" the released electrons before they relax and rejoin the locally ionized atoms or molecules, thereby selectively forming a plasma at or proximal to the pigmented cells. Other pigmented targets located in the tissue, which may be external to cells, can also be irradiated to promote selective absorption of energy and plasma generation.

In still further exemplary embodiments of the present disclosure, a method for selectively producing plasma in pigmented regions of biological tissue can be provided. The exemplary method can include directing and focusing electromagnetic radiation (e.g. optical energy) as described herein onto a plurality of focal regions within the tissue using an optical arrangement, such that the optical energy is selectively absorbed by pigmented regions to generate some local ionization via thermionic emission of electrons. The beam intensity and local dwell time should be sufficiently large to allow further energy to be absorbed by the freed electrons, leading to further ionization by the excited electrons and a subsequent chain reaction (sometimes referred to in physics literature as an "electron avalanche") to locally form a plasma in the tissue These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Figure 1:
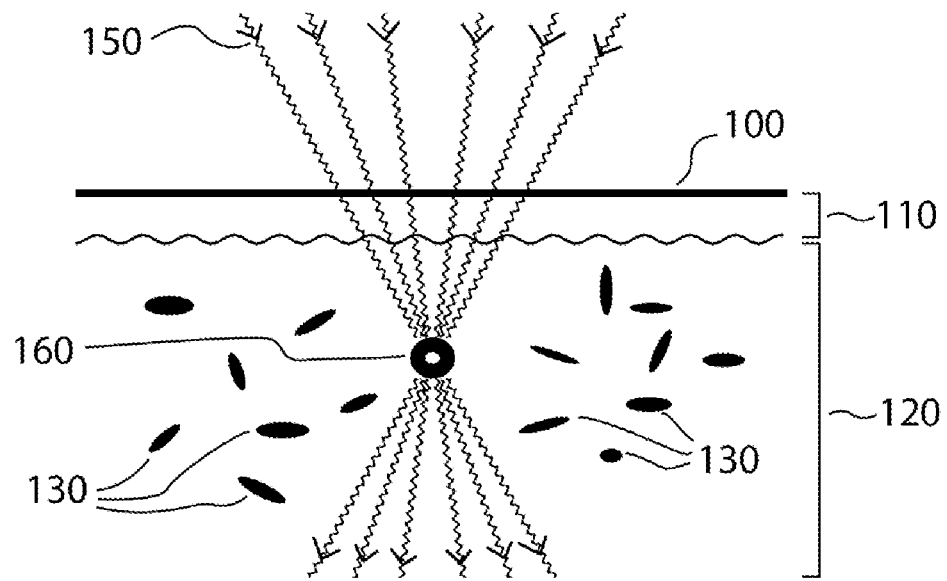
FIG. 1 is a representative side view of one or more beams of radiation being focused into pigmented dermal tissue.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

Exemplary embodiments of the present disclosure can provide devices and methods for selectively producing plasmas in biological tissue using thermionic plasma initiation. Thermionic plasma initiation is a thermophysical process, distinct from dielectric breakdown, that starts with heating of a material, liberating some thermal electrons. The electrons rapidly re-combine with the ionized molecules from which they came, but under appropriate conditions they can also absorb incoming photons from the laser/energy source to initiate a plasma. Thermionic plasma initiation is based in part on the mechanism of linear absorption of light by a chromophore, and therefore can occur preferentially at sites of enhanced light absorption within a complex material such as living tissue. Thermionic plasma initiation typically requires a high power density, but this power density is usually much lower (e.g., by orders of magnitude) than that needed for dielectric breakdown. Therefore, in a heterogeneous material such as biological tissue, it is possible for a pulsed laser to initiate thermionic plasma under appropriate conditions at the sites where a chromophore exists within the tissue.

Thermionic plasma initiation depends on the ability to liberate thermal electrons from a chromophore and/or nearby molecules. Some molecules have weakly-bound electrons, which are more likely to be liberated when the material is heated, while molecules without weakly-bound electrons are less likely to liberate thermal electrons. In tissue, melanin is an example of a chromophore with many weakly-bound electrons. Melanin is also a strong chromophore over most of the optical spectrum. As such, melanin can be a preferential site for thermionic plasma formation when exposed to sufficient power density, e.g., from a pulsed laser. In contrast, plasma formation via dielectric breakdown does not depend on the presence of a chromophore.

The efficacy of heating a chromophore to initiate a thermionic plasma depends in part on energy density. The energy of a laser pulse is the time integral of laser power. Femto- and pico-second laser pulses, which can initiate dielectric breakdown in very short time intervals, tend to have an energy density that is below that needed for thermionic plasma initiation because of the very short duration of the pulses. Longer pulse durations, even those in the microsecond domain (a million times longer than the femtosecond domain), can initiate thermionic plasma formation under certain conditions when a suitable chromophore is present and the local power density is sufficiently high. The pulse energy is preferably focused to a sufficient degree to provide a sufficiently high local energy density in the tissue.

In certain embodiments of the present disclosure, electromagnetic radiation (optical energy) such as, e.g., optical energy, at one or more particular wavelengths can be focused into the tissue, where the optical energy can optionally be pulsed and/or scanned, such that the optical energy is selectively absorbed by regions of the tissue containing chromophores. Such linear absorption of the optical energy can lead to local thermionic emission of electrons. With appropriate selection of optical energy parameters and beam geometry, further irradiation of the tissue region can lead to further energy absorption by the emitted electrons, followed by local plasma formation and non-linear absorption of energy. This procedure can produce intense heat, local expansion, stress waves such as strong acoustic or shockwaves, and/or chemical reactions due to the plasma in the chromophore-containing region of tissue while generating relatively little energy absorption and associated tissue damage in unpigmented regions.

General focusing of a laser beam below the surface of a material, such as a living tissue, is known in the art as a technique for providing a high power density at the focal region, which can be adjusted to a given depth below the material surface, e.g., using lenses and/or other optical components. For example, confocal laser microscope imaging of living human skin can provide detailed images of tissue at the depth of a focal plane by scanning a laser beam focal point within the tissue.

In exemplary embodiments of the present disclosure, a laser-induced plasma can be generated at a focal spot within tissue, based in part on selective absorption of the optical energy by chromophores that may be present; a pulsed laser beam can also be scanned or moved to produce a plurality of laser-induced plasmas as the focal spot changes location within the tissue. Thermionic plasma formation requires a threshold level of power and energy density at the site where a chromophore is present, as noted herein above. For thermionic plasma formation, a laser focal region within the tissue can be scanned to initiate plasma formation at a depth defined by the laser focus geometry, and such plasma can be selectively formed only at sites where a chromophore is present. In this manner, a focused, scanned laser can be used to selectively damage chromophore sites within a well-defined region (e.g., within one or more focal planes) inside the tissue.

Normal skin contains the chromophore melanin within the epidermis and hair follicles, and not within the dermis. Pathological conditions can, however, lead to melanin deposition in the dermis. These conditions include post-inflammatory hyperpigmentation and melasma. Also not present in normal dermis, but present in some conditions, are exogenous chromophores, such as, e.g., pigment particles such as those in tattoo inks. Various precipitates that may be present in tissues after drug treatment can also act as chromophores. Such precipitates can include, e.g., gold, silver, tetracyclines, iron, amiodarone, chlorpromazine and others. Other chromophores that may be present in biological tissue include, e.g., sebaceous glands, subcutaneous fat, hair bulbs, lipids in cell membranes, fat surrounding organs, blood vessels, and certain drug components.

For certain treatments and conditions, it can be desirable to effect the removal of such chromophore particles in the dermis, without substantial harm to the overlying epidermis. Certain exemplary embodiments of this disclosure can provide methods and apparatus for such chromophore removal that include, e.g., scanning the focal spot or region of a pulsed laser in one or more planes within the dermis and below the epidermis, under conditions that selectively generate thermionic plasma formation at the sites of chromophore within the focal plane, without causing such plasma formation within the overlying epidermis. Such plasma formation can also generate local selective damage to the dermal tissue by physical and/or chemical mechanisms resulting from the plasma formed at the site of chromophores in the dermis.

In practice, a scanned focal region or multiple focal regions of near infrared radiation capable of initiating thermionic plasma can be achieved up to a depth in skin of approximately 2 mm (2000 µm), as described herein. The epidermis is nominally 0.1 mm thick (except for palms and soles of the feet, which are generally thicker), such that a focal plane of a laser having appropriate electromagnetic, temporal, and optical properties can be achieved within the dermis and below the epidermis, enabling thermionic plasma formation selectively at and/or proximal to chromophore sites in the dermis. After physical and/or chemical damage to the target chromophore sites in the skin or tissue, biological processes such as fluid transport, lymphatic uptake, phagocytosis and/or enzyme digestion can ultimately transport, remove or digest the altered chromophore sites from the dermis. Also, biological cells containing or proximal to such chromophores that are irradiated to generate a plasma can be damaged, modified, or killed, e.g., via necrosis or apoptosis.

Shorter wavelengths of optical radiation (e.g., towards the violet and ultraviolet end of the optical spectrum) tend to be scattered more by the non-homogeneous structures of skin tissue than longer wavelengths. Such scattering can reduce the effective penetration depth of optical energy directed onto the tissue, and also inhibit focusing of a beam of optical energy into a small focal region as described herein. In general, the near-infrared portion of the optical spectrum (the so-called optical window) is capable of deeper penetration in to tissue, because these longer wavelengths undergo less scattering. When dermal melanin is the target chromophore, wavelengths between about 600 and 1100 nm are preferable for effective penetration into skin tissue together with good absorption by melanin. In certain embodiments, shorter wavelengths including ultraviolet, blue, green, and yellow regions of the optical spectrum could be used. The choice of one or more wavelengths of the optical energy can be based on, e.g., the desired focal depth(s) and the type(s) and concentrations of chromophore present at one or more depths in the tissue.

The focal region size/width, quality, and length along the beam axis of a focused laser beam directed into a biological tissue can be determined by such factors as the laser beam divergence, laser mode structure, numerical aperture of the beam focusing optics, aberrations of the focusing optics, coupling of the beam into tissue at the tissue surface (e.g. surface reflection and refraction effects), and optical scattering properties of the tissue.

"Rayleigh range" is the term used to describe the extent or length of a focal region along the optical axis. For example, the Rayleigh range can describe the size of a focal region along the depth or z axis for a beam directed into skin tissue. The Rayleigh range is affected by such factors, e.g., as the laser source divergence, wavelength of the optical energy, laser mode(s), original diameter of the beam prior to convergence by optical elements, and numerical aperture of the focusing system. For example, a highly-convergent beam, where the outer boundaries of the beam converge at a relatively large angle as the beam reaches the focal region (and diverge at a similar angle beyond the focal region), can exhibit relatively small Rayleigh length. A smaller focused convergence angle would lead to a larger Rayleigh range, as the beam converges and diverges slowly with respect to distance along the beam axis. Typically, the Rayleigh range is several times larger than the transverse focal spot diameter.

By varying the focusing optical design and/or laser mode structure, a wide variety of laser focal spots can be produce, which can be characterized by geometrical parameters such as spot size or width (e.g., a characteristic dimension perpendicular to the axis of the beam in the focal region), and the Rayleigh range (e.g., a dimension of the focal region along the longitudinal axis of the beam). The appropriate dimensions of a focal region for selectively initiating plasmas in biological tissue (via thermionic emission) can be selected based on factors such as the size of the chromophores being targeted, the pulse energy and power of the optical energy source (which, together with the size of the focal region will affect local power and energy densities), the Rayleigh range (which will further affect the range of depths that can be scanned within a volume of tissue in a particular time interval), etc. For example, dermal pigmentation, whether from melanin, tattoos or drugs, is typically contained in cells that are themselves about 10 µm in diameter. Accordingly, a spot size/diameter of about this size or larger may be desirable in certain embodiments, e.g., to irradiate entire cells to facilitate energy absorption by any chromophores within the cells. In other embodiments, a smaller spot size may be used, for example, if small areas are being irradiated or if scanning speeds are sufficiently high.

An exemplary embodiment of the disclosure that describes plasma formation in melanin-rich regions of the dermis will now be described in some detail. Further embodiments of the disclosure can produce selective plasma formation in other biological tissues, where the selectivity is governed by other chromophores that may be present in the tissue such as, e.g., hemoglobin, certain tattoo inks, or the like.

An exemplary schematic side view of a section of skin tissue is shown in FIG. 1. The skin tissue includes a skin surface 100 and an upper epidermal layer 110, or epidermis, which is typically about 60-120 µm thick over much of the human body. The dermal thickness is about 2-3 mm over most of the body, but it can be slightly thicker in other parts of the body, such as the soles of the feet, and is particularly thin in other sites such as the eyelids. The underlying dermal layer 120, or dermis, extends from below the epidermis 110 to the deeper subcutaneous fat layer (not shown). A population of pigmented cells or regions 130 that contain excessive amounts of melanin is shown in FIG. 1. Such dermal pigmentation is typical of a dermal (or 'deep') melasma condition in skin.

In exemplary embodiments of the present disclosure, a beam of electromagnetic radiation (optical energy) 150 (e.g., optical energy) can be focused into one or more focal regions 160 that can be located within the dermis 120. The optical energy 150 can be provided at one or more appropriate wavelengths that can be preferentially absorbed by melanin. The optical energy wavelength(s) can be selected to provide some degree of enhanced absorption of the energy by the pigmented regions 130 relative to other unpigmented regions of the dermis 120.

In one exemplary embodiment of the present disclosure, a Yb fiber laser having a wavelength of 1060 nm can be used to generate the optical energy. In further embodiments, optical energy having wavelengths between about 600 nm to 1100 nm may be provided with sufficient focusing and/or appropriate power and fluence, as described herein, to achieve sufficient intensity and selectivity of absorption by chromophores in the tissue. As described throughout the present specification, certain combinations of optical energy wavelength, local power density or intensity, and local irradiation times can be combined to produce the desired effects.

Figure 2:
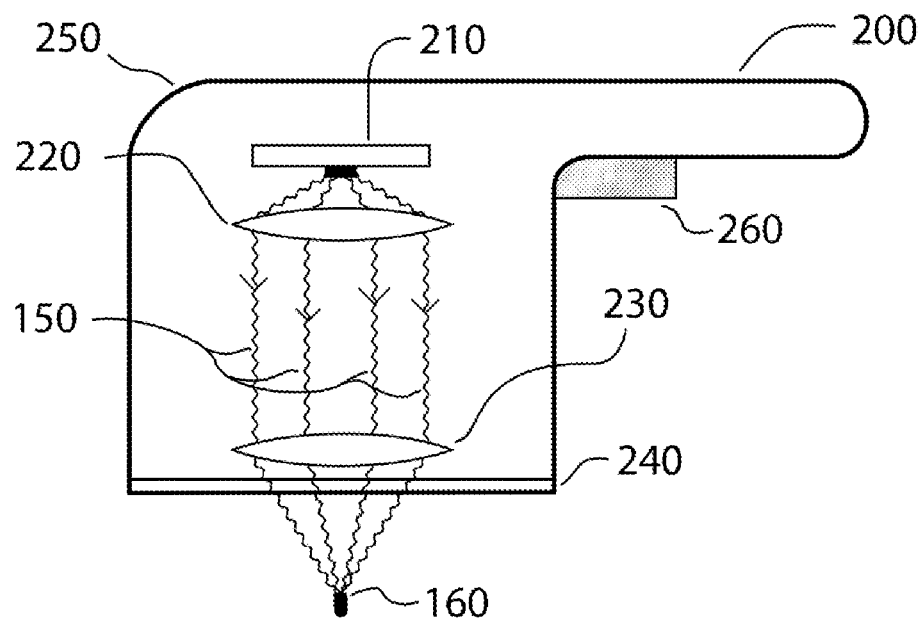
FIG. 2 is a cross-sectional side view of an exemplary apparatus in accordance with exemplary embodiments of the present disclosure.

In further exemplary embodiments of the present disclosure, an apparatus 200, schematically illustrated in a diagram of FIG. 2, can be provided to selectively generate plasma in tissue by irradiating it with optical energy 150, e.g., optical energy. For example, the apparatus 200 can include a radiation emitter arrangement 210, and an optical arrangement that can be provided between the radiation emitter arrangement 210 and the target tissue to be treated. For example, the optical arrangement can include a first lens arrangement 220 and a second lens arrangement 230. These exemplary components can optionally be provided in a handpiece 250 or other housing or enclosure. The apparatus 200 can further include a contact surface configured to contact the surface 100 of the tissue being treated. In one embodiment, the contact surface 240 can include the second lens arrangement 230. In this embodiment, the contact surface 240 may be convex, such that it provides local compression of the underlying tissue when the apparatus 200 is placed on the tissue being treated.

An actuator arrangement 260 can be provided to control the operation of the apparatus 200, e.g., to activate and/or turn off the emitter arrangement 210, control or adjust certain operational parameters of the apparatus 200, etc. A power source (not shown) for the radiation emitter arrangement 210 can be provided. For example, the power source can include a battery provided within the handpiece 250, an electrical cord or other conductive connection provided between the emitter arrangement 210 and an external power source (e.g. an electrical outlet or the like), etc.

The radiation emitter arrangement 210 can include, e.g., one or more optical energy sources (including a pulsed laser such as, e.g., flashlamp-pumped pulsed lasers, Q-switched lasers, mode-locked pulsed lasers, a Q-switched fiber laser, or a diode-pump solid-state laser). These lasers can sometimes be powered by a diode laser), optical fibers, waveguides, or other components configured to generate and/or emit optical energy 150 and direct it toward or onto the optical arrangement 220, e.g., onto the first lens arrangement 220. In further exemplary embodiments, the radiation emitter arrangement 210 can include distal ends of one or more waveguides (e.g., optical fibers) (not shown), where the waveguides can be configured or adapted to direct optical energy 150 from an external optical energy source, such as a laser (not shown), toward or onto the first lens arrangement 220.

In further exemplary embodiments of the present disclosure, the electromagnetic radiation (optical energy) 150 can be focused into one or more focal regions 160 that can be located within the tissue 120, as shown schematically in FIGS. 1 and 2. The exemplary optical arrangement can be configured to provide one or more highly-convergent beams of optical energy 150, where each such beam can be emitted from a lower portion of the apparatus 200 and converge to a narrower focal region 160 located at a particular distance below the lower surface of the apparatus 200, e.g., below the lower surface of the contact surface 240. Such convergence of the optical energy 150 can produce a high local fluence and intensity within the focal region 160, while irradiating the overlying tissue (e.g. epidermis 110 and upper portion of the dermis 120 in FIG. 1) at a lower fluence. In certain embodiments, the focal region 160 can be located at or very close to the lower surface of the contact surface 240, which can thus provide high-intensity irradiation of the surface region of the tissue contacting the contact surface 240.

The first lens arrangement 220 can be adapted and/or configured to direct optical energy 150 from the emitter arrangement 210 towards or onto the second lens arrangement 230. The first lens arrangement 220 can include, e.g., one or more lenses, reflectors, partially- or fully-silvered mirrors, prisms, and/or beam splitters. For example, the first lens arrangement 220 can be configured to collimate or align the optical energy 150 emitted from the emitter arrangement 210 onto the second lens arrangement 230, as shown in FIG. 2. The first lens arrangement 220 can include, e.g., an objective lens or the like.

The second lens arrangement 230 can be configured and/or adapted to receive optical energy 150 from the first lens arrangement 220, and direct it into one or more focal zones 160 within the dermis 120, as shown in FIG. 1, or into other tissues. For example, the first lens arrangement 220 can be a collimating lens, and the second lens arrangement 230 can serve as a focusing lens that includes, e.g., a single objective lens as shown in FIG. 2, one or more plano-convex lenses or cylindrical lenses, or the like. Various exemplary optical arrangements can be used to produce one or more focal regions 160. Some embodiments of such optical arrangements are described in more detail herein below. In certain embodiments, a single optical arrangement (which may include 2 or more lenses, reflectors, prisms, or the like) may be used to focus the optical energy 150 into a focal region 160.

As shown in FIG. 2, the highly-convergent beam of optical energy 150 is relatively "spread out" as it is passes through the contact surface 240 (e.g., as it enters the surface 100 of the skin tissue when the apparatus 200 is placed on the skin to irradiate it). Geometrical, temporal, and power characteristics of the optical energy 150 can be selected as described herein, such that the fluence and intensity of the optical energy 150 at and near the skin surface 100 are sufficiently low to avoid unwanted heating and damage to the tissue overlying the focal region 160. The optical energy 150 can then be focused to a sufficient intensity and fluence within the focal zone 160 to facilitate significant absorption of the optical energy 150 by pigmented regions 130 within or proximal to the focal region 160. In this manner, exemplary embodiments of the present invention can target pigmented regions 130 within the dermis 120 to selectively heat them, and to further generate a plasma, without generating unwanted damage to the overlying tissue and surrounding unpigmented tissue.

Exemplary beam convergent angles of about 70-80 degrees are illustrated in FIGS. 1 and 2. In general, the convergent angle can be about 40 degrees or greater, e.g., even about 90 degrees or larger. Such non-narrow convergence angles can generate a large local intensity and fluence of optical energy 150 at the focal region 160, while the corresponding fluence in the overlying (and underlying) tissue regions may be lower due to the beam convergence and divergence. It should be understood that other convergence angles are possible, and are within the scope of the present disclosure.

Accordingly, the effective numerical aperture (NA) of the second lens arrangement 230 is preferably large, e.g., greater than about 0.5, such as between about 0.5 and 0.9, when the apparatus 200 is used to generate a plasma in tissue regions below the tissue surface. The numerical aperture NA is generally defined in optics as NA=n sin θ, where n is the refractive index of the medium in which the lens is working, and θ is one-half of the convergence or divergence angle of the beam. The optical energy 150 enters the lens through surrounding air, which has an index of refraction of about 1. Thus, an exemplary convergent half-angle θ of the beam of optical energy towards the focal region 160, corresponding to a NA value between about 0.5 and 0.9, can be between about 30 and 65 degrees. Thus, the exemplary range of the total convergence angle can be between about 60 and 130 degrees. The NA may be smaller, e.g., when surface regions of the tissue are being irradiated, as there is little or no overlying tissue that could be damaged inadvertently.

Larger values of the effective NA can provide a larger convergence angle, and a corresponding greater difference in the local beam intensity and fluence between the tissue surface 100 and the focal region 160. Accordingly, a larger NA value can provide a greater "safety margin" by providing less intense irradiation levels to the overlying tissue than to the pigmented regions 130, thereby reducing the likelihood of generating thermal damage in the overlying tissue. However, a larger NA value can decrease the size of the focal region 160 relative to the area of the incoming optical energy beam, which can thereby irradiate a relatively smaller treatment volume of pigmented tissue within the dermis 120. Such smaller treatment volumes can reduce the efficiency of treating large areas of skin in a reasonable time. Exemplary NA values between about 0.5 and 0.9 can thus provide a reasonable compromise between safety factor and treatment efficiency, although slightly larger or smaller values of the NA may be used in certain embodiments (e.g., by adjusting other system parameters appropriately, such as beam power, scanning speed, etc.).

A width of the focal region 160 (e.g., a "spot size") can be small, e.g., less than about 100 μm, for example, less than 50 μm, or less than 10 μm. In general, the focal region can be defined as the volumetric region in which the optical energy 150 is present at a highest intensity. For example, the focal region 160 may not be present as an idealized spot because of such factors as scattering of the optical energy 150 within the tissue, aberrations or nonidealities in the optical components (e.g. lenses and/or reflectors), variations in the path of the incident rays of optical energy 150, etc. Further, the focal region 160 can be spread over a small range of depths within the tissue, as shown schematically in FIGS. 1 and 2. In general, the size and location of the focal region relative to the apparatus 200 can be determined or selected based on properties and configuration of the optical arrangement (e.g., the first and second lens arrangements 220, 230), the characteristics of the optical energy 150 provided by the emitting arrangement 210, and optical properties of the tissue being treated.

In certain exemplary embodiments, the width of the focal region 160 (e.g., the "spot size") can be less than 50 μm, e.g., smaller than 10 μm. The focal spot diameter or spot size can be generally defined as the smallest diameter of an actual focused (e.g., convergent) beam, which converges as it enters the focal region and diverges as it exits the focal region. By varying parameters, components, and configuration of the focusing optical arrangement and/or laser mode structure, a wide variety of laser focal spot sizes can be produced. A minimum theoretical beam focal spot size can be determined by optical diffraction and the number of optical modes present in the laser output, and is referred to as the diffraction-limited focal spot size. Typically, this minimum spot size is several times the wavelength of the corresponding light. For example, using a 1060 nm single-mode fiber laser (which has good focusing properties), the diffraction-limited focal spot diameter for an optical system focusing into the dermis would be less than about 5 μm. In practice, effects such as optical scattering in the tissue and aberrations of optical components produce focal spots greater than this diffraction-limited minimum.

Dermal pigmentation, such as melanin, tattoo inks, or drug components, is typically contained within cells, which are themselves about 10 μm in diameter. The laser focal spot diameter can be greater than or less than the diameter of such target cells, depending on desired results and the laser/optics being used. A laser having lower power output can be focused to relatively smaller sizes to achieve sufficient energy and power densities. Alternatively, a higher-powered laser can thermionically initiate a plasma with a relatively larger spot size. Such larger spot sizes can, e.g., be scanned over a given area or volume of tissue in a shorter time to selectively produce plasma at chromophore sites in the volume of tissue.

For example, a theoretical lower for the spot size can be approximated as $1.22\lambda/NA$, where $\lambda$ is the wavelength of the electromagnetic radiation and NA is the numerical aperture of a lens. For a wavelength of about 1060 nm and a NA of 0.5, the theoretical minimum spot size is about 2.6 microns. The actual spot size (or width of the focal region 160) can be selected as being small enough to provide a sufficiently high power density or density of optical energy 150 in the focal zone 160 (sufficient to initiate thermionic emission and subsequently generate a plasma). For example, for a given pulsed laser source having a particular pulse duration and peak (or average) pulse power (or total pulse energy), a smaller spot size will result in a larger intensity (or power density). Based on geometrical considerations, the power and energy densities of a particular optical beam pulse in a focal region are inversely proportional to the square of the focal spot size (or, inversely proportional to the focal spot area).

For a particular exemplary NA value of the focusing lens arrangement 230, the beam radius at the surface can be estimated as the focal depth multiplied by the tangent of the half-angle of convergence provided by the focusing lens. As an example, an NA value of 0.5 corresponds to a convergence half-angle of about 30 degrees, for which the tangent is 0.577. For an exemplary focal depth of 200 microns into the tissue, the radius of the converging optical energy beam at the skin surface 100 is about 115 microns (0.577×200), such that the total beam width at the surface is about 230 microns. The local intensity is inversely proportional to the local cross-sectional area of the beam for a particular beam power. Accordingly, for a spot size (focal region width) of 20 microns, the ratio of fluence at the focal region to that at the skin surface (ignoring absorption between the surface and focal spot) is about (230/20), or about 130:1. The actual fluence ratio may be somewhat less due to absorption of some of the optical energy between the tissue surface and the focal region. Nevertheless, this exemplary calculation indicates that a focusing lens having a high NA can generate a relatively low intensity in the surface regions of the tissue as compared to the intensity in the focal region.

In further exemplary embodiments of the present disclosure, a plurality of such focal regions 160 can be generated simultaneously by the exemplary apparatus. In still further embodiments, the focal region(s) 160 may be scanned or traversed through the portions of tissue containing chromophores to irradiate larger volumes of the tissue in a reasonable time, as described in more detail herein.

In certain exemplary embodiments for selectively generating plasma in skin tissue exhibiting dermal melasma, the depth of the focal region 160 below the skin surface 100 can be up to about 2000 μm. In some exemplary embodiments of the present disclosure, an exemplary focal depth below the skin (or other tissue) surface can be between about 5 μm and about 1000 μm, which permits a range of treatment depths that can be achieved without excessive scattering or absorption of energy above the focal region 160. In further exemplary embodiments of the present disclosure, the depth of the focal region 160 can be between about 120 μm and 400 μm, e.g., between about 150 μm and 300 μm. These latter exemplary depth ranges can generally correspond to the observed depths of pigmented regions 130 in skin that exhibits dermal melasma. The exemplary focal depth can correspond to a distance from the bottom of the apparatus 200 (e.g., the lower surface of the contact surface 240) and the focal region 160 of the optical energy 150, because the contact surface 240 may flatten out the underlying tissue when placed on the skin surface 100. Accordingly, the depth of the focal region 160 within the skin may be selected or controlled based on a configuration of the optical arrangements 220,230 within the housing 250.

In various exemplary embodiments of the present disclosure, the optical energy 150 can be collimated (e.g., rays within the optical energy beam are substantially parallel to one another), convergent, or divergent between the first lens arrangement 220 and second lens arrangement 230. In still further exemplary embodiments, the radiation emitter arrangement 210 and/or components of the optical arrangement (e.g., the first lens arrangement 220 and/or the second lens arrangement 230) can be controllable or adjustable such that the path of the optical energy 150 can be varied. Such exemplary variation in the path of the optical energy 150 can provide corresponding variations in the depth, width, and/or location of the focal region 160 within the tissue being irradiated when the apparatus is held stationary with respect to the tissue.

For example, the position and/or angle of the optical energy 150 can be shifted relative to the optical axis of a lens in the second lens arrangement 230. Alternatively or additionally, the convergence or divergence of the optical energy 150 entering or within the optical arrangement can be varied. Such variations in the optical energy geometry and/or path can provide variations in the depth and/or lateral position of the focal region(s) 160. In this manner, larger volumes of the tissue can be irradiated while the apparatus 200 is held stationary over the area of tissue being treated. Such exemplary variation of the focus region characteristics can facilitate treatment of a plurality of depth ranges and/or locations within the tissue containing chromophores (including, but not limited to, pigmented cells or vascular structures).

Exemplary adjustment and/or alteration of the geometry and/or path of the optical energy 150 can be achieved, e.g., using one or more translators, movable mirrors, beam splitters and/or prisms, or the like, which may be coupled to the radiation emitter arrangement 210, the first lens arrangement 220, and/or the second lens arrangement 230. In further embodiments, the apparatus 200 can be translated over the area of tissue being treated to irradiate larger volumes of the tissue at one or more depths, thereby targeting a greater number of chromophore-containing regions within a larger tissue volume. Such translation can be done using a controllable translating apparatus, or alternatively such translation can be done manually, e.g., by having a user hold the apparatus in hand and moving it over the tissue surface. Combinations of manual and automated translational movement can be provided in still further embodiments.

In further exemplary embodiments, the exemplary apparatus 200 in FIG. 2 can include a sensor arrangement for detecting the velocity and/or position of the apparatus 200 relative to the tissue being treated, e.g., while it is manually scanned over the tissue, and the data sent to a control arrangement (not shown) that can affect output parameters of the laser and/or translating apparatus, if present. For example, a mechanical or optical motion sensing arrangement, similar to that found in a computer mouse device, can be used to track velocity and/or position of the apparatus 200 during use. Feedback control based on velocity and/or position data can be used, e.g., to affect parameters such as pulse duration, pulse frequency, pulse energy, etc. Appropriate controls can be implemented based on application of conventional control techniques, together with the various parameter ranges and phenomena described herein, to avoid unwanted tissue damage including, but not limited to, plasma formation away from chromophores, or excessive energy irradiation of overlying tissues (e.g. in the epidermis). Similar tracking devices have been successfully employed for device control in hand-scanned fractional lasers used for dermatological treatments (e.g., Reliant Fraxel® laser systems).

Figure 3A:
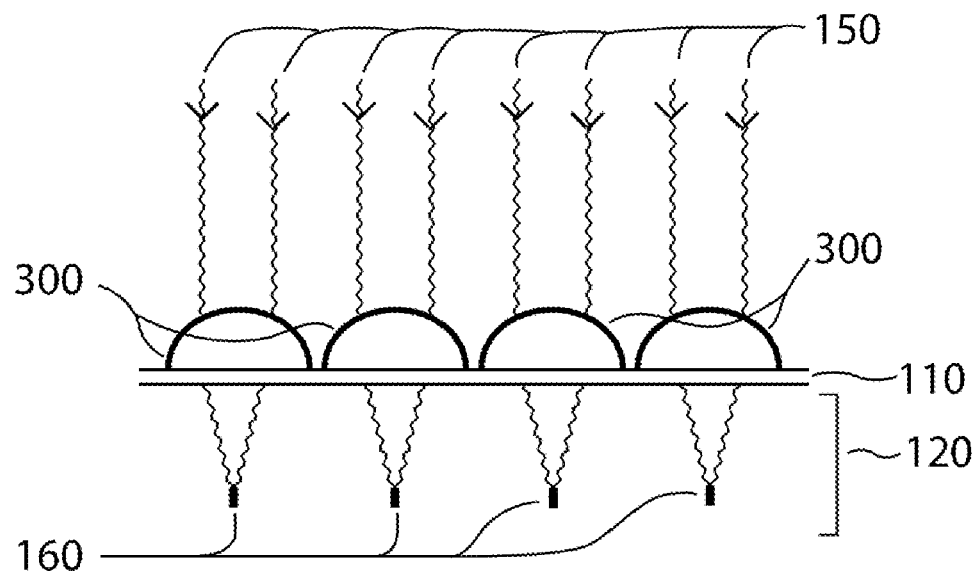
FIG. 3A is a side view of an arrangement of micro-lenses that can be used with certain exemplary embodiments of the present disclosure.

In one embodiment of the present disclosure, the second lens arrangement 230 can include a plurality of micro-lenses 300, e.g., as provided in a schematic side view of the exemplary configuration illustrated in FIG. 3A. For example, the micro-lenses 300 can include any conventional type of convergent lenses, e.g., convex lenses, or plano-convex lenses such as those shown in FIG. 3A. The micro-lenses 300 can be configured to focus optical energy 150 into a plurality of focal regions 160 within the underlying dermis 120 or other tissue, as illustrated in FIG. 3A.

Each of the micro-lenses can have a large NA (e.g., between about 0.5 and 0.9), such that the optical energy 150 converges from a relatively wide area at or near the surface 100 of the skin or other tissue (with a relatively low intensity/power density and fluence) to a small width (with higher intensity/power density and fluence) in the focal region 160 within the dermis 120 or other tissue. Such optical properties can provide a sufficient intensity of optical energy 150 within the focal region 160 to initiate plasma formation, while avoiding areas or volumes of high intensity away from the volume of tissue containing chromophores (e.g. pigmented cells 130), thereby reducing likelihood of damaging overlying, underlying, and/or adjacent volumes of unpigmented skin tissue.

Figure 3B:
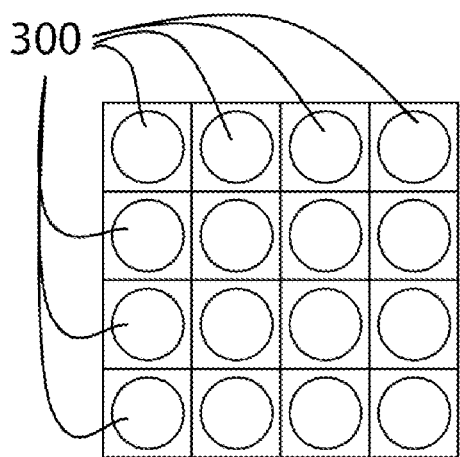
FIG. 3B is a top view of a first exemplary arrangement of the micro-lenses shown in FIG. 3A.
Figure 3C:
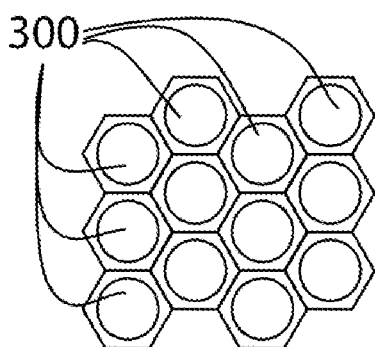
FIG. 3C is a top view of a second exemplary arrangement of the micro-lenses shown in FIG. 3A.

The micro-lenses 300 can be provided in any geometric pattern such as, but not limited to, a substantially square or rectangular array, such as that shown in the top view of such exemplary configuration in FIG. 3B. According to further exemplary embodiments of the present disclosure, the micro-lenses 300 can be provided in a hexagonal array, as shown in FIG. 3C. Other exemplary patterns and/or shapes of the micro-lenses 300 can be provided in still further exemplary embodiments. A width of the micro-lenses 300 can be small, e.g., between about 1 mm and 3 mm wide. The exemplary micro-lenses 300 that are slightly wider or narrower than this can also be provided in certain exemplary embodiments. The array of micro-lenses 300 can itself be moved or scanned, to provide a dense array (or a continuous region) of tissue volume irradiated by focal spots over time, in the focal plane(s) of the lens array.

In additional embodiments of the present disclosure, the radiation emitter arrangement 210 and/or the first lens arrangement 220 can be configured to direct a single wide beam of optical energy 150 (such as, e.g., that shown in FIG. 2) over the entire array of micro-lenses 300 or a substantial portion thereof. Such exemplary configuration can generate a plurality of focal regions 160 in the tissue simultaneously. In further exemplary embodiments, the radiation emitter arrangement 210 and/or the first lens arrangement 220 can be configured to direct a plurality of smaller beams of optical energy 150 onto individual ones of the micro-lenses 300. According to still further exemplary embodiments, the radiation emitter arrangement 210 and/or the first lens arrangement 220 can be configured to direct one or more smaller beams of optical energy 150 onto a portion of the array of micro-lenses 300, e.g. onto a single micro-lens or a plurality of the micro-lenses 300, and the smaller beam(s) can be scanned over the array of the micro-lenses 300, such that a plurality of the focal regions 160 can be generated sequentially or non-simultaneously in the tissue being irradiated.

Figure 3D:
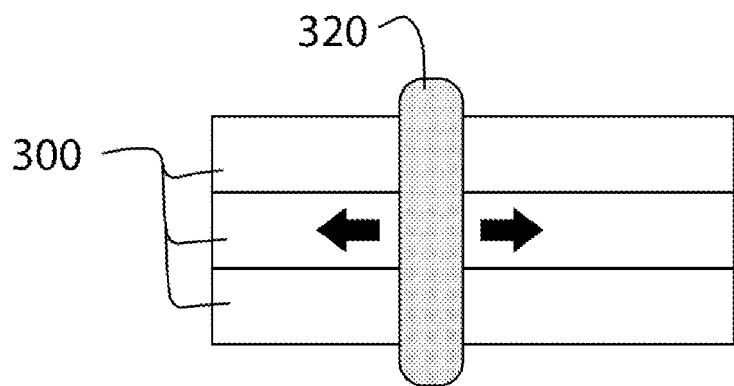
FIG. 3D is a top view of an exemplary arrangement of cylindrical micro-lenses that can be used with certain exemplary embodiments of the present disclosure.
Figure 3E:
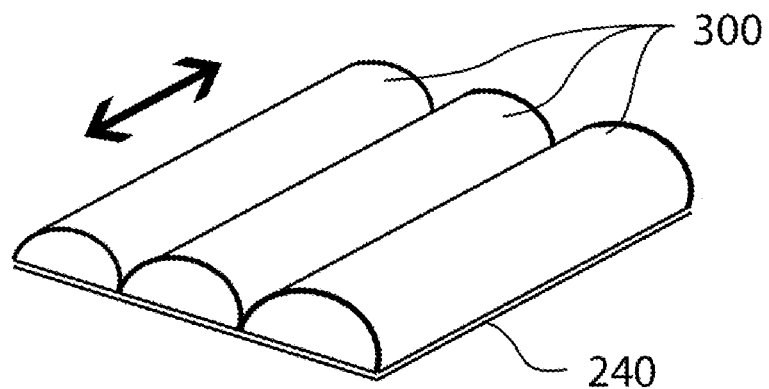
FIG. 3E is a perspective view of the exemplary arrangement of cylindrical micro-lenses shown in FIG. 3D.

In yet further exemplary embodiments of the present disclosure, the micro-lenses 300 can include cylindrical lenses, for example, convex cylindrical lenses or plano-convex cylindrical lenses, e.g., as shown in an exemplary top view in FIG. 3D and exemplary angled view in FIG. 3E. In the context used herein, 'cylindrical' does not necessarily require the rounded surface of the lens to be circular; it may have an elliptical or other smooth but non-circular profile in certain embodiments. Such cylindrical lenses can have a uniform profile in any cross-section that is perpendicular to the longitudinal axis of the lens.

A width of the cylindrical micro-lenses 300 can be small, e.g., between about 1 mm and 3 mm wide. The length of the cylindrical micro-lenses 300 can be between about 5 mm and 5 cm, e.g., between about 5 mm and about 2 cm. This width and length can be selected based on such factors as the total power emitted by the radiation emitter arrangement 210, the overall size of the array of micro-lenses 300, etc. In certain exemplary embodiments, cylindrical micro-lenses 300 that are slightly shorter or longer and/or slightly narrower or wider can be provided.

In certain exemplary embodiments of the present disclosure, any of the exemplary arrays of the micro-lenses 300 can be provided on (or formed as part of) the contact surface 240, as illustrated in FIG. 3E. Such configuration can facilitate placement of the micro-lenses 300 close to the tissue surface, and also facilitate a more precise depth of the focal regions 160 within the tissue, e.g., when the contact surface 240 contacts the tissue surface during use.

In further exemplary embodiments of the present disclosure, the radiation emitter arrangement 210 and/or the first lens arrangement 220 can be configured to direct a single wide beam of optical energy 150 (such as that shown in FIG. 2) over the entire array of cylindrical micro-lenses 300 or a substantial portion thereof. Such exemplary configuration can simultaneously generate and/or produce a plurality of the focal regions 160 within the tissue 120 that are elongated in one direction (e.g. along the longitudinal axis of the cylindrical micro-lenses 300) and narrow (e.g., less than about 100 µm wide, less than about 50 µm wide, or even less than about 10 µm wide) in a direction orthogonal to the longitudinal axis of the cylindrical micro-lenses 300. Such "line-focused" optical energy 150 can be used to more efficiently irradiate larger volumes of the tissue, e.g., when the exemplary apparatus 200 is scanned over the area of tissue being treated, for example, in a direction substantially orthogonal to (or optionally at some other angle to) the longitudinal axis of the cylindrical micro-lenses 300.

According to yet additional exemplary embodiments of the present disclosure, the radiation emitter arrangement 210 and/or the first lens arrangement 220 can be configured to direct one or more smaller beams of optical energy 150 onto one or more of the cylindrical micro-lenses 300. For example, the optical energy 150 can be directed onto one or more cylindrical micro-lenses 300, e.g., over an elongated area 320 such as that shown in FIG. 3D. The radiation emitter arrangement 210 and/or the first lens arrangement 220 can be further configured to scan or traverse the irradiated area 320 over the cylindrical micro-lenses 300 (for example, using one or more movable mirrors, prisms, waveguides, or the like in the optical arrangement), e.g., along the longitudinal directions indicated by the arrows shown in FIGS. 3D and 3E (or back and forth along such direction), such that a plurality of the elongated focal regions 160 are progressively generated in the dermis 120 during the scan. Such scanning of the optical energy 150 can produce an irradiated focal region 160 having a shape of an extended line within the dermis 120. The apparatus 200 can also be traversed laterally over the region of skin being treated, e.g., in a direction not parallel to the longitudinal axes of the cylindrical micro-lenses 300, during the irradiation such that the elongated focal regions 160 can travel through the dermis 120 and irradiate a larger volume of tissue. For example, as described herein such lateral traversal can be between about 5 mm/sec and 5 cm/sec. The scanning speed of the optical energy beam along the axes of the cylindrical can be larger, e.g., greater than about 10 cm/sec, to provide a more uniform irradiation of such larger volumes of tissue. The scan rate of the optical energy 150 along the cylindrical lens axes, traversal speed of the apparatus 200 over the skin, power of the optical energy emitter arrangement 210, and width of the focal region 160 can be selected to provide a local fluence generated within portions of the dermis 120 by the elongated focal region 160 that is within the exemplary fluence ranges described herein.

Figure 3F:
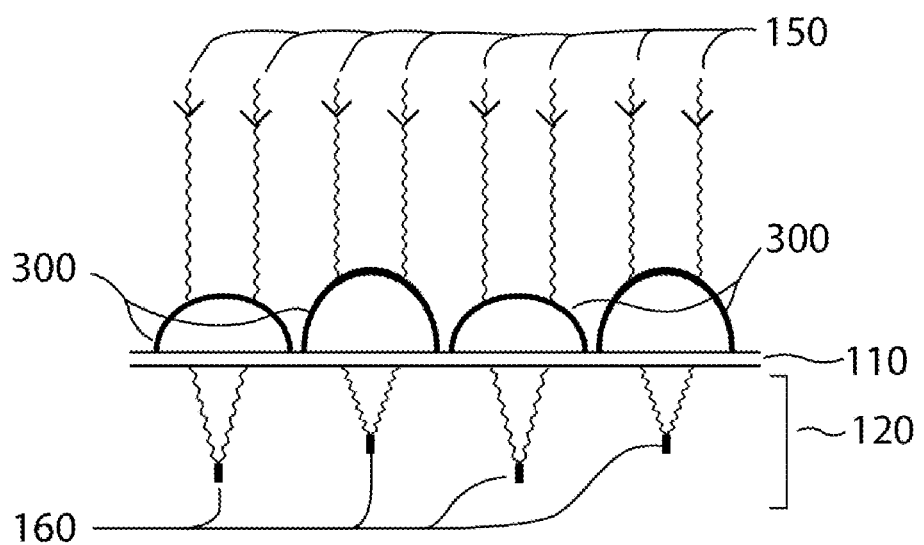
FIG. 3F is a side view of a further exemplary arrangement of micro-lenses that can be used with further exemplary embodiments of the present disclosure.

In yet further exemplary embodiment of the present disclosure, some of the cylindrical or spherical micro-lenses 300 can have different NA values, different sizes or radii, and/or different effective focal lengths, e.g., as shown in the exemplary schematic diagram in FIG. 3F. The different focal depths of the micro-lenses 300 below the skin surface 100 can be, e.g., between about 120 µm and 400 µm, for example, between about 150 µm and 300 µm. Such exemplary variations in the focal lengths can produce focal regions 160 at different depths, which can result in irradiation of larger volumes of the dermis 120 when the exemplary apparatus 200 is translated over the area of skin being treated, thereby targeting a greater number of pigmented cells 130 that may be present (e.g., irradiating both shallower and deeper pigmented cells 130 in the dermis 120).

In one exemplary embodiment, the radiation emitter arrangement 210 and/or the first lens arrangement 220 can be further configured to vary the incident angle of the optical energy 150 as it is directed onto the second lens arrangement 230 or the micro-lens array 300. Such variation in angle can direct the focal region 160 from a plurality of pulses into a plurality of locations without translating the apparatus 200 or any lenses with respect to the tissue 100. Such variation of the incident angle can provide more uniform irradiation of the tissue during scanning, by irradiating a plurality of spots for each fixed location of the apparatus 200 and/or lenses with respect to the tissue 100.

In another exemplary embodiment of the disclosure, the first lens arrangement 220, the second lens arrangement 230, and/or the micro-lens array 300 can be configured (e.g. using actuators or the like) to controllably vary the focal distance between the apparatus 200 and the focal region 160. Such variation in the focal distance can direct the focal region 160 from a plurality of pulses to a plurality of depths at a single location without translating the apparatus 200 or any lenses with respect to the tissue 100. This type of scanning pattern can be used to irradiate multiple depths (z-values) at each location during a scanning procedure before advancing the focal region to another (x-y) location on the tissue. The sequential depths irradiated at a location can vary from deeper to shallower in one embodiment (by decreasing the focal distance while irradiating a particular x-y location). Alternatively, the focal distance can be varied from shallower to deeper (by increasing the focal distance while irradiating a particular x-y location). Either depth sequence may be used, and selected based on other factors such as the effect of irradiation on deeper or overlying regions of tissue, the depth distribution of chromophores in the tissue, etc. These embodiments in which the focal depth is varied at a single x-y location represent an alternative to the exemplary scan pattern illustrated in FIG. 4, in which the focal region 160 is scanned in a raster pattern or the like at a fixed focal depth (e.g., within a single x-y plane) and then the focal depth is varied to scan another x-y plane at a different depth.

The window or contact surface 240, if present, can be configured and/or structured to contact the surface 100 of the area of skin being treated. The lower surface of the window 240 can be substantially planar, or it may be convex or concave in further embodiments. The window 240 can provide certain benefits during operation of the apparatus 200. For example, the window 240 can facilitate precise positioning of the first and second optical arrangements 220, 230 relative to the skin surface 100, which can facilitate accurate control, selection and/or variation of the depth(s) of the focal region(s) 160 within the skin.

The window 240 can further stabilize the soft skin tissue while it is being irradiated by the apparatus 200, which can facilitate control and uniformity of the irradiation profile. Pressure provided by the window 240 on the skin surface 100 can also blanche (or remove some blood from) the volume of skin tissue being irradiated, thereby reducing the amount of pigmented structures present locally (e.g. blood-filled vessels containing hemoglobin). Such blanching can facilitate increased selectivity of absorption of the optical energy 150 by pigmented cells 130 while reducing a risk of unwanted damage to blood vessels.

In exemplary embodiments of the disclosure, the window 240 can be cooled, e.g., by pre-cooling it prior to using the apparatus 200 or by active cooling using a conventional cooling arrangement (e.g. a Peltier device, a conductive cold conduit, or the like). In other embodiments, the tissue itself can be cooled prior to irradiation, e.g., using a cryospray or contact cooling with a cold object. Such cooling can facilitate protection of upper portions of the tissue from unwanted damage and/or pain sensation while the pigmented regions within the tissue are being irradiated to produce a plasma therein.

A refractive index coupling fluid or gel can be used to reduce optical losses and aberrations as the laser beam(s) pass from the optical focusing apparatus into the tissue. For example, human skin has a refractive index of about 1.5 in the optical region of 600-1100 nm, and its surface is rough, such that a beam of light encounters the skin at a range of local incidence angles. Air has a refractive index of 1.0, such that reflection and refraction is high. By applying a fluid or gel material with refractive index closer to that of the skin, the losses and aberrations are less. An analogous situation and solution relating to a use of focused lasers for reflectance confocal microscopy of skin was described, e.g., in M. Rajadhyaksha et al., "In vivo confocal scanning laser microscopy of human skin: melanin provides strong contrast," *J Invest Dermatol.*, 104(6), 946-52 (June 1995).

According to certain exemplary embodiments of the present disclosure, the window 240 can be provided as part of the second lens arrangement 230. For example, the second lens arrangement 230 can include a single plano-convex lens or a plurality of plano-convex lenses, such as those shown in FIGS. 3A and 3D. Such lenses can be affixed to or formed as part of the window 240. The lower (planar) surface of such lenses can provide the benefits of the window 240 as described herein, e.g., precise positioning of the second lens arrangement 230 relative to the skin surface 100 to control depth of the focal regions 160.

The actuator arrangement 260 can be configured to activate and/or control the radiation emitter arrangement 210 and/or an external optical energy source that provides radiation to the radiation emitter arrangement 210, such that the irradiation characteristics of an area of tissue by the optical energy 150 can be controlled. The radiation emitter arrangement 210 and/or the exemplary apparatus 200 can further include a conventional control arrangement (not shown) that can be configured to control and/or adjust the properties of the optical energy 150 directed onto the tissue being treated.

For example, the apparatus 200 can include one or more sensors (not shown) configured to detect contact of the apparatus 200 with the skin surface 100 and/or speed or displacement of the apparatus 200 over the skin surface 100 during use. Optical sensors can also be provided to detect the present of sparks or flashes that indicate generation of a plasma in the irradiated tissue. Such exemplary sensors can generate signals capable of varying properties of the optical energy 150, e.g., by varying the power emitted by the radiation emitter arrangement 210 based on the translational speed of the apparatus 200, by turning off the source(s) of optical energy 150 when the apparatus 150 is stationary relative to the tissue surface 100, etc. Such sensors and control arrangements can be provided as a safety feature, e.g. to prevent excessive irradiation and unwanted damage to the tissue being treated, and are generally known in the art. For example, an optical sensor can be used to adjust parameters of the optical energy source for a given focal geometry and scanning/translational speed such that plasma generation in pigmented regions is just initiated. Such control can avoid excessive plasma formation and/or formation of plasma in tissue that does not contain chromophores. Further variations of such conventional sensing and/or control arrangements can be used in embodiments of the present disclosure. In general, local irradiation times (or "dwell times") should be sufficiently long to selectively generate a plasma in the tissue following the initial linear energy absorption by the chromophores. The dwell time can be estimated, e.g., as the time it takes the full width of the focal region to pass over a particular point in the tissue at a given scan speed. Accordingly, the dwell time can be calculated as the optical energy beam width or diameter divided by the scan speed.

Limiting irradiation times (dwell times) at a particular focal region location can be achieved in various ways. In one exemplary embodiment, the radiation emitter arrangement 210 can be configured to provide discrete pulses of optical energy 150 into the focal regions 160. The interval between such pulses of optical energy can be, e.g., on the order of about 50 milliseconds or more even if the location of the focal region is moving through the skin tissue at a relatively slow speed of a few mm/s. These exemplary parameters can result in a distance between focal regions 160 irradiated by successive pulses of, e.g., about 50-100 microns, which can be greater than a width of the focal region 160 itself. Accordingly, such general parameters can facilitate spatial and temporal separation of the successive irradiated focal regions 160, such that local thermal relaxation can occur and buildup of excess heat can be avoided. The spot size, pulse duration, and/or total pulse energy can be selected based on the principles and guidelines described herein, using simple calculations, to provide a sufficient intensity within the focal region 160 to generate a plasma in the pigmented structures 130 while maintaining a sufficiently small dwell time (e.g. less than about 1-2 ms) to avoid damaging unpigmented tissue.

In further exemplary embodiments of the present disclosure, the focused radiation 150 can be scanned over a region of skin containing chromophores (such as, e.g., pigmented lesions or the like), such that the focal region(s) 160 may irradiate a large number of the pigmented regions with sufficient intensity to form a plasma. Such scanning can be performed with any of the embodiments described herein. The scanning can be done manually, e.g., using a conventional method of translating a handpiece over an area of skin to be treated. Alternatively, the apparatus 200 can optionally be coupled to a translating arrangement that can be configured to automatically move the apparatus (or certain components thereof) over an area of tissue to be treated. Such automatic translation can be provided as a pre-set pattern or as a random or semi-random path over the skin. In still further embodiments, one or more of the optical components (e.g. the first and/or second lens arrangement 220, 230) and/or the radiation emitter arrangement can be translated within the housing 250, such that the focal region(s) 160 can translate within the tissue while the housing 250 is held in a single position relative to the tissue.

Average scan speeds (or ranges of such speeds) can be determined based on the general exemplary guidelines described herein. For example, for a particular spot size (which can be determined primarily by the properties of the optical arrangement), the local dwell (irradiation) time can be estimated as the spot size/width divided by the translational speed. As noted herein, such dwell time is preferably less than about 1-2 milliseconds to avoid local heat buildup and unwanted thermal damage of unpigmented tissue. Accordingly, a minimum scan speed can be estimated as the width of the focal region 160 divided by 1 millisecond. For example, a spot size of 10 microns (0.01 mm) would correspond to a minimum scan speed of 0.01 mm/0.001 seconds, or about 10 mm/sec (1 cm/sec). Scan rates for line-focused beams (e.g., produced by directing an optical energy beam onto a cylindrical lens) can be estimated in a similar manner, e.g., where the width of the focal line corresponds to the width of the focal region and the scan speed is in a direction perpendicular to the focal line, or for other scanning configurations.

For a pulsed laser source, the scan speed can be selected based at least in part on the pulse energy and repetition rate, such that the total energy deposited into the target area can be controlled. For a pulsed laser source, the local dwell time would correspond to the duration of the pulse, if the scan rate is low enough compared to the pulse duration that the focal region does not move appreciably (e.g., it moves only a fraction of the focal region width, such as half the spot width or less) during the pulse. As an example, with a pulse duration of 100 ns, a repetition rate of 50 khz, and a scan speed of 200 mm/s, there is a pulse of energy deposited every 4 microns along the scan path, and the focal region moves only about 0.02 microns during the pulse. Further, such scan speed and pulse repetition rate would lead to about, we would expect about 2-3 pulses of energy to be received by a 10 um cell, each pulse having a local dwell time of 100 ns.

A power output of the radiation emitter arrangement 210 can be selected based on several factors including, e.g., the optical energy wavelength, the number, sizes, and/or depths of the focal regions 160, optical characteristics and geometry of the first and second lens arrangements 220, 230, etc. The power output can be selected such that the fluence in the focal region 160 is sufficiently high to damage pigmented cells 130 that absorb the optical energy 150 for short exposure times, while fluence at other depths (e.g., in the epidermis 110) is sufficiently low to minimize or avoid unwanted damage there.

Based on some experimental observations, a local intensity (power density) within the focal region 160 that may be sufficient to generate a plasma in melanin-containing structures (e.g., pigmented cells) can be about $10^{10}$ W/cm$^2$ or more, for example, between about $10^{10}$ W/cm$^2$ and $10^{11}$ W/cm$^2$ for optical energy 150 having a wavelength of about 1060 nm. A corresponding dwell time for local irradiation can be on the order of $10^{-5}$ sec (e.g., 10 microseconds). This range of effective local beam intensity can increase with increasing scanning/translational speed of the focal region in the tissue, to maintain a consistent local irradiation (dwell) time. Larger or smaller intensity values may also be provided when using faster or slower scan speeds, in further exemplary embodiments. For example, a thermionic plasma in melanin may be initiated at lower power density, e.g., as low as about $10^8$ W/cm$^2$, if other parameters such as absorption efficiency (which depends in part on wavelength of the optical energy) and energy density (which also depends in part on pulse duration) are selected appropriately. The local dwell time can preferably remain on the order of tens of microseconds in such embodiments.

Typical scan speeds for a handpiece that is manually translated over an area of skin to be treated can be, e.g., on the order of about 5 mm/sec to about 5 cm/sec. Such speeds correspond to traversing a distance of 5 cm (about 2 inches) in about 1-10 seconds. Accordingly, for a handpiece that is translated manually over the skin to irradiate portions of the dermis as described herein, the power output and focal geometry of the apparatus 200 can be selected to provide a power density and dwell time at the irradiated locations within the dermis that is within the general range described herein.

Such exemplary power calculations can be based on the entire output of the laser diode being focused into one focal region. If the output from a single source of optical energy is focused onto a plurality of focal regions (e.g., when using an optical splitter or a wide beam directed onto a plurality of micro-lenses), then the power output of the optical energy source should be multiplied by the number of focal spots 160 to achieve the same power density within each focal region 160. Optical energy 150 can be provided as a continuous wave (CW) or optionally as a plurality of pulses. Alternatively, a plurality of optical energy sources (e.g. laser diodes or the like) can be provided to generate a plurality of irradiated focal regions 160 simultaneously, with the appropriate power level for each optical energy source being estimated as described above. In certain embodiments, if one or more optical energy beams are scanned over the focusing lens arrangement 230, the power of the optical energy source can be selected based on the lens properties, scan speed, etc. to provide power densities and dwell times at pigmented locations of the tissue irradiated by the focal regions 160 that are within the general ranges described herein.

In certain exemplary embodiments of the present disclosure, the radiation emitter arrangement 210 can include a plurality of optical energy emitters (e.g., laser diodes or lasers with separate waveguides). Such emitters can be provided in a linear array, such that they lie substantially along one or more straight lines. In further exemplary embodiments, the emitters can be arranged in a two-dimensional pattern, which can provide further patterns of optical energy 150 directed onto the first lens arrangement 220. As described above, the power output of each emitter can be selected using a routine calculation based on the focal spot size and scan speed to generate a local power density and dwell time for each focal zone 160 that is within the preferred range described herein.

The apparatus 200 shown in FIG. 2 illustrates one exemplary configuration, and other embodiments using various combinations and/or configurations of similar components can also be used in further embodiments. For example, different numbers and/or types of optical arrangements 220, 230 and/or emitter arrangements 210 can be used to provide irradiation characteristics and focal regions 160 within the dermis 120 as described herein. In certain embodiments, the apparatus 200 can be provided in a shape factor similar to that of a handheld razor, with the radiation emitter arrangement 210 provided as one or more laser diodes, optical arrangements 220, 230 provided in the "head" of the razor, and a power source (e.g. one or more conventional alkaline cells or the like) provided in the handle. Other form factors can also be used in further embodiments of the disclosure such as, e.g., apparatus shapes that are more suitable for being translated by a motorized or automated translating apparatus.

One or more exemplary parameters of the apparatus 200 can be selected and/or adjusted once the other ones are known to provide effective irradiation of the pigmented cells 130 to selectively form a plasma at the pigmented regions, as described herein. For example, the exemplary apparatus 200 having known geometry (e.g. spot size or focal line width, and NA) of the lens arrangements 220, 230 (and internal scanning speed of optical energy beams, if present), and a particular wavelength of optical energy 150 can be provided. The power of the optical energy source(s) can then be selected based on a target range of scanning speeds of the apparatus 200 over the area to be treated to achieve appropriate local power densities and dwell times. For example, the exemplary apparatus 200 can be traversed over an area of tissue at a speed between about 1-5 cm/s, which corresponds approximately to the speed at which a conventional razor is traversed over skin during shaving. Using these exemplary parameters and the number of passes to be made over the treatment area, the local dwell time of the focal region(s) 160 can be estimated, and a power output of the radiation emitter arrangement 210 can then be selected or adjusted to provide an effective local power density within the focal region 160 as described herein. Such calculations are routine and can be done by a person of ordinary skill in the art.

In still further exemplary embodiments, two consecutive pulses can be used to selectively form a plasma at or proximal to a chromophore as described herein. For example, a laser having a modulated laser intensity can be used, or two or more lasers having different parameters and focused to the same region, can be used to selectively initiate thermionic emission at a chromophore under a first set of local energy conditions, and subsequently "pump" the thermal electrons under a second set of local energy conditions to produce the local plasma. The absorptive heating of melanin is a linear process, whereas pumping of the thermal electrons into an electron avalanche to form and sustain a plasma is a non-linear process. The thermal relaxation time of a melanosome, the primary structure that biological melanin is associated with in nature, is several hundred nanoseconds. The laser used to selectively produce a plasma in tissue, as described in certain embodiments herein, can have a pulse duration on the order of about 100 ns, which is less than the thermal relaxation time for melanosomes. These timescales allow the melanosomes to be efficiently heated to induce emission of thermal electrons, but operate well above the short femto- and pico-second ranges associated with dielectric breakdown. The thermal relaxation of time of a pigmented cell is much longer, about 10-100 μs.

Accordingly, based on the principles described herein, a laser pulse having a duration on the order of, e.g., 10 μs, could be used to selectively heat the pigmented cells to liberate some electrons via thermionic emission. A second optical energy pulse having appropriate parameters, as described herein, including a pulse duration on the order of approximately 100 ns, could then be focused to irradiate the same pigmented cells and "pump" the released electrons before they relax and rejoin the locally ionized atoms or molecules, thereby forming a plasma at the pigmented cells. Other pigmented targets located in the tissue, which may be external to cells, can also be irradiated to promote selective absorption of energy and plasma generation.

In further exemplary embodiments of the present disclosure, a method for selectively producing plasma in pigmented regions of biological tissue can be provided. The exemplary method can include directing and focusing electromagnetic radiation 150 as described herein onto a plurality of focal regions 160 within the dermis 120 using an optical arrangement, such that the optical energy 150 is selectively absorbed by pigmented regions 130 to generate some local ionization via thermionic emission of electrons. The beam intensity and local dwell time should be sufficiently large to allow further energy to be absorbed by the freed electrons, leading to further ionization by the excited electrons and a subsequent chain reaction (sometimes referred to in physics literature as an "electron avalanche") to form a plasma in the tissue.

Example 1

An animal study using an exemplary spot-focused laser device and model system were used to test the efficacy of selective plasma formation in skin tissue using optical radiation. The study was performed on a female Yucatan pig, as described below.

First, a deep-melasma condition was simulated by tattooing the dermis using a melanin-based ink. The ink was prepared by mixing synthetic melanin at a concentration of 20 mg/mL in a 50:50 saline/glycerol solution. The resulting suspension was then agitated prior to being injected into approximately 1"×1" test sites on the animal subject using a standard tattoo gun, at a depth range of about 200-400 μm. Each test site was provided with a darker black tattooed border using India ink to facilitate identification of the various test sites.

An exemplary melasma treatment system was constructed based on exemplary embodiments of the present disclosure described herein, which includes a Q-switched 1060 nm Yb-fiber laser with an average power of up to 10 W, operating at a pulse rate between 20 kHz and 100 kHz and a pulse duration of 100 ns. The laser was mounted on an x-y scanning platform. The measured focal spot size was approximately 4 μm. The collimated output of the fiber laser was focused with an effective focal length of 8 mm and a numerical aperture (NA) of 0.5.

A table of exemplary scanning parameters used to establish selective formation of plasmas in biological tissue is shown below in Table 1. The laser power was either 2 or 4 W, the raster line speed of the focal spot was between 50 and 800 mm/s, the spacing between adjacent raster scan lines (which determines the overall coverage of each plane) ranged between 0.0125 and 0.05 mm. These parameter ranges were selected to cover a range in which some parameter sets produced a plasma, as evidenced by visible white sparks and audible popping sounds, and others did not. In general, plasma formation was not observed at scanning rates of about 400 mm/s or more at these power levels.

The energy and scanning parameters shown in Table 1 represent exemplary testing parameters used to evaluate the functioning of the prototype apparatus described herein and to refine approximate parameter combinations for further study. Plasma formation was observed at scan speeds less than about 100 mm/s for these power levels of 2 and 4 watts, whereas higher scan speeds did not generally result in observed plasma formation.

Figure 4:
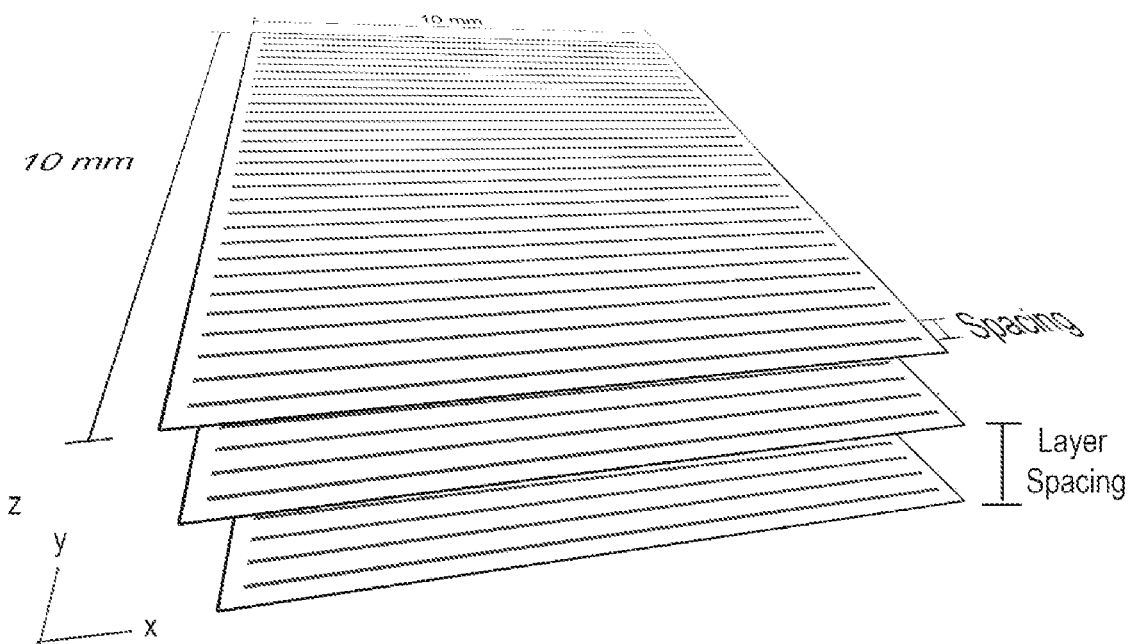
FIG. 4 is a schematic illustration of a scan pattern that can be used with exemplary embodiments of the present disclosure.

Exemplary system parameters and procedure for producing visible effects in biological tissue were as follows: The scanner was used to scan the laser beam over a 1 cm×1 cm area within each melanin-tattooed test site at a speed of 200 mm/s, which tended to produce evidence of plasma formation. Different test scans were run with laser power outputs of 1 W, 2 W, 3 W, 4 W, and 10 W. Multiple depths were scanned in each test site, with the beam focal region scanned in a raster scan pattern at a single focal depth before changing the focal depth and repeating the raster scan pattern. Most test treatments were performed at a 50 kHz pulse repetition rate, with some tests performed at a 20 kHz for comparison. A schematic illustration of the scan pattern used for 3 separate depths is shown in FIG. 4.

The distance between successive focal-depth planes was about 50 μm, and a 'rest' interval of about 4-5 minutes was provided between area raster scans at each focal depth, to allow the tissue to cool. Between successive scans at different depths, rubbing alcohol was sprayed onto the treated area and massaged in order to help dissipate the white cavitation that was observed to form when the laser interacts with tissue layers containing melanin. Without such alcohol rubbing, this white film was observed to take significantly longer to dissipate on its own (e.g., about 10-15 minutes as compared to about 4-5 minutes with the alcohol rubbing).

Figure 5:
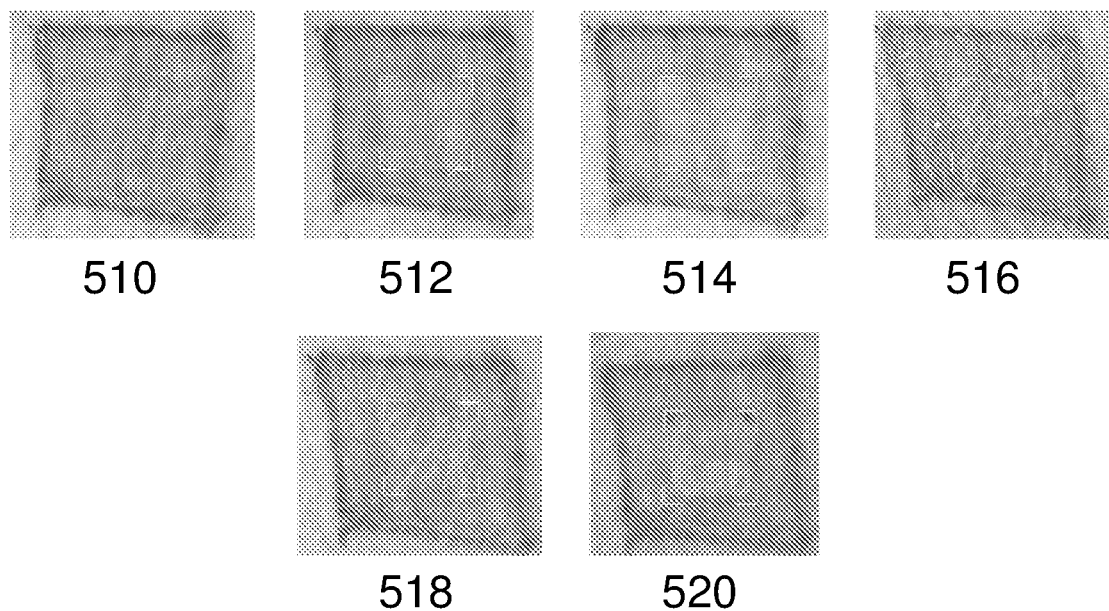
FIG. 5 shows a set of exemplary images, obtained at different times, of a region of pig skin that was irradiated in accordance with certain exemplary embodiments of the present disclosure.

Exemplary results of an exemplary treatment of a melanin-tattooed test site in accordance with exemplary embodiments of the present disclosure are shown in FIG. 5. The Yb-fiber laser was set to an average of 2 W power output, with a pulse repetition rate of 50 kHz and a scan speed of 200 mm/s. The distance between adjacent raster lines was 12.5 µm, and 6 different depths were irradiated, ranging from 300 to 550 µm at 50-µm intervals.

For example, image 510 provided in FIG. 5 shows the test site just prior to scanning with the laser apparatus, and image 512 shows the test site just after the scan was completed. Images 514, 516, 518, and 520 illustrate the appearance of the test site at 2 hours, 1 day, 1 week, and 4 weeks, respectively, after the irradiation treatment. Immediate lightening of the irradiated region was observed post-treatment, and it persisted 4 weeks later.

TABLE 1

Exemplary parameters for raster scanning of the optical energy beam focal region over each constant-depth plane within the test areas. The rectangular raster pattern is illustrated in FIG. 4.
Yb-fiber laser (1060 nm)

| Power (watt) | Speed (mm/s) | Spacing (mm) | Coverage | Layers | Relative Energy Delivered | Time (min) |
|---|---|---|---|---|---|---|
| 2 | 50 | 0.05 | 25% | 2 | 50% | 6.666667 |
| 2 | 100 | 0.0125 | 100% | 2 | 100% | 20.8 |
| 4 | 400 | 0.0125 | 100% | 2 | 50% | 16 |
| 4 | 400 | 0.025 | 50% | 2 | 25% | 8 |
| 4 | 400 | 0.05 | 25% | 2 | 12.5% | 4 |
| 4 | 800 | 0.0125 | 100% | 2 | 50% | 13.3 |
| 4 | 800 | 0.025 | 50% | 2 | 25% | 6.66 |
| 4 | 800 | 0.05 | 25% | 2 | 12.5% | 3.33 |
| 2 | 800 | 0.0125 | 100% | 2 | 25% | 13.33 |
| 2 | 800 | 0.025 | 50% | 2 | 12.5% | 6.66 |
| 2 | 800 | 0.05 | 25% | 2 | 6.25% | 3.33 |
| | | | | | Total Time | 102.13 |

Example 2

Figure 6:
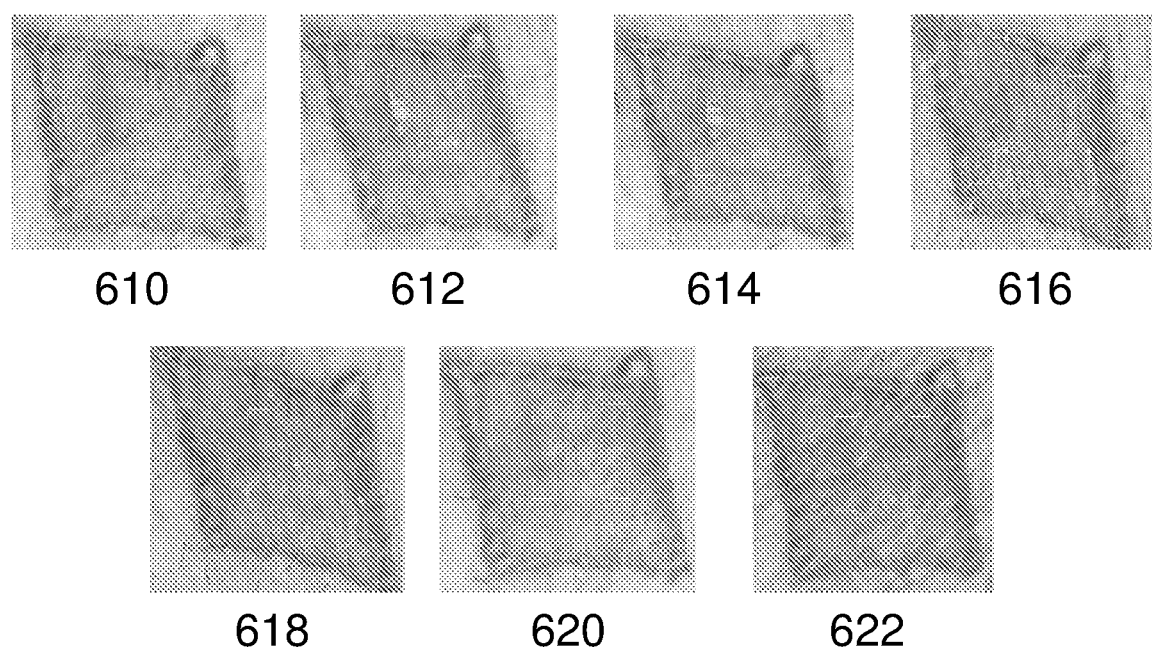
FIG. 6 shows a further set of exemplary images, obtained at different times, of a region of a pig skin that was irradiated in accordance with further exemplary embodiments of the present disclosure.

FIG. 6 shows a further scanned melanin-tattooed test site that was irradiated using the general scan parameters indicated above (e.g., a scan rate of 200 mm/s, a repetition rate of 50 kHz, and six (6) sequential scanned layer depths of 550, 500, 450, 400, 350, and 300 µm, and a distance between adjacent scan lines in each plane of 25 µm), with a fiber laser output of 1 W, at various times, in accordance with further embodiments of the present disclosure. Image 610 in FIG. 6 shows the test site just prior to a scanned irradiation using the laser apparatus, and image 612 shows the test site just after the scan was completed. Images 614, 616, 618, 620, and 622 illustrate the appearance of the test site 610 at 1 hour, 3 days, 1 week, 2 weeks, and 4 weeks, respectively, after the irradiation treatment. No plasma formation was observed at this lower power output level.

Example 3

Figure 7A:
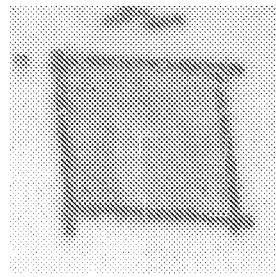
FIG. 7A shows a further set of exemplary images, obtained at different times, of a region of the pig skin that was irradiated over a range of depths in accordance with still further exemplary embodiments of the present disclosure.
Figure 7A:
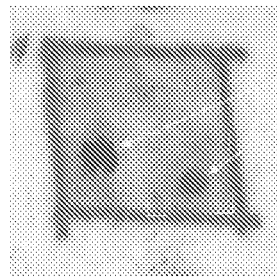
Figure 7A:
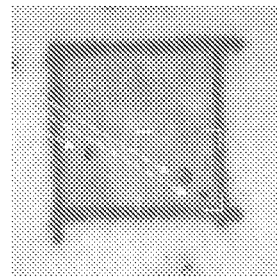
Figure 7B:
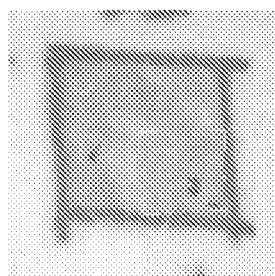
FIG. 7B shows a further set of exemplary images, obtained at different times, of the same region of pig skin shown in FIG. 7A that was irradiated at deeper depths and 2 weeks after the first irradiation scan shown in FIG. 7A, in accordance with still further exemplary embodiments of the present disclosure.
Figure 7B:
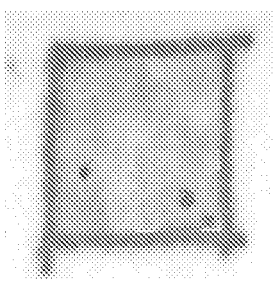
Figure 7B:
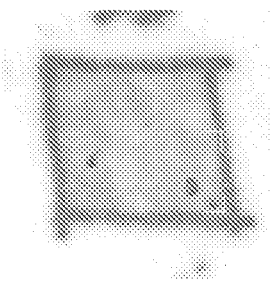

FIGS. 7A and 7B show images of a melanin-tattooed test site that was scanned twice, over two sessions spaced two weeks apart. Both irradiation treatments used a fiber laser with an average power output of 6 W and a pulse repetition rate of 20 kHz. The first scan session targeted more superficial layers (300 um to 550 um) whereas the second scan session targeted deeper layers (550 um to 850 um).

In particular, FIG. 7A illustrates exemplary results of the first scanned irradiation treatment. Image 710 in FIG. 7A shows the test site just prior to the first scanned irradiation using the laser apparatus, image 712 shows the test site just after the first scan was completed, and image 714 shows the test site 24 hours after the first scan was completed. Images 716, 718, and 720 provided in FIG. 7B show the appearance of the test site 710 just prior to, immediately following, and 24 hours following the second irradiation treatment, respectively. This second deeper irradiation treatment was performed 2 weeks after the first scanning treatment. Plasma formation (in the form of small sparks and popping noises) was observed at this intermediate power output level.

Example 4

Figure 8A:
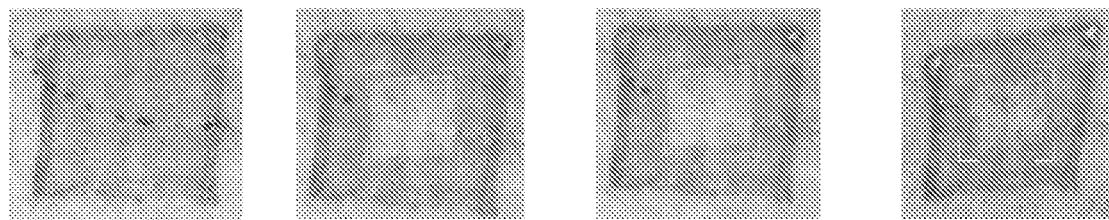
FIG. 8A shows a further set of exemplary images, obtained at different times, of a region of pig skin that was irradiated in accordance with yet further exemplary embodiments of the present disclosure.
Figure 8A:
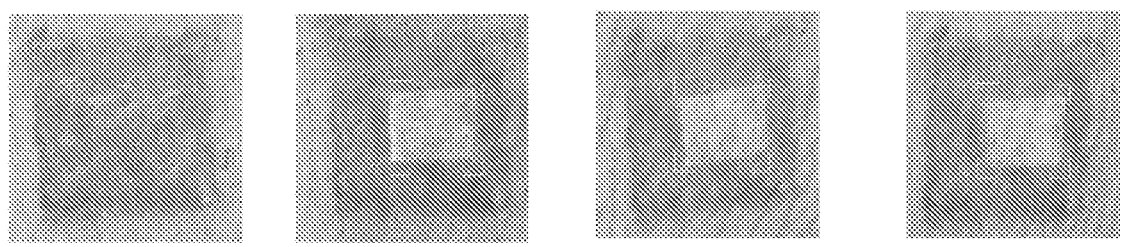

More immediate skin whitening effects were observed at higher power outputs. For example, a tattooed test site was scanned at a fiber laser power output of 10 W, with other scan parameters matching those used to obtain the results illustrated in FIGS. 7A and 7B. Whitening of the scanned area in the center of the tattooed region was observed immediately following the scanning procedure, as shown in FIG. 8A. The observed plasma was more intense at this higher power level, indicating a correlation between (peak) power level and plasma intensity under conditions where plasmas are generated selectively in tissue.

General guidelines for generating plasma selectively at the sites of melanin chromophores can be estimated from the various test scans performed. For example, with a spot size of 4 um, an average fiber laser power output of 4 W, a pulse duration of 100 ns, and a repetition rate of 50 kHz (which produced visible plasma effects with some whitening of the skin at later times, as shown in FIG. 5), the local peak power density can be calculated as approximately $6.37 \times 10^9$ W/cm$^2$, and the peak power is about 800 W.

At the higher end of applied power density (e.g., 10 W average power and 20 kHz repetition rate, corresponding to the conditions of FIG. 8A), the peak power density is about $3.98 \times 10^{10}$ W/cm$^2$ and the corresponding peak power is about 5 kW. These higher power levels led to more immediate whitening of the tissue and a more intense visible plasma.

For the scan speeds used (typically 200 mm/s), the pulse duration of 100 ns is sufficiently short that the focal spot does not move by more than a few nanometers before the pulse is switched off. At a scan speed of 200 mm/s, each 10 mm scan line in the takes 0.05 seconds to complete. At a pulse rate of 50 kHz, there are 2500 pulses per scan line, such that the distance between successive pulses is about 4 µm. Because the spot width used is 4 µm and the distance between the centers of adjacent pulses along the scan line is also 4 µm, this set of scan parameters generates an essentially continuous train of pulses that are just touching each other (e.g., a continuous scanned line with little overlap). Accordingly, for melanophages or other chromophore sites having a diameter or width of about 10 µm, each melanophage would be subjected to roughly 2-3 pulses. With the exemplary pulse duration of 100 ns, the total local dwell (exposure) time for such melanophages is about 250 ns.

Example 5

Figure 8B:
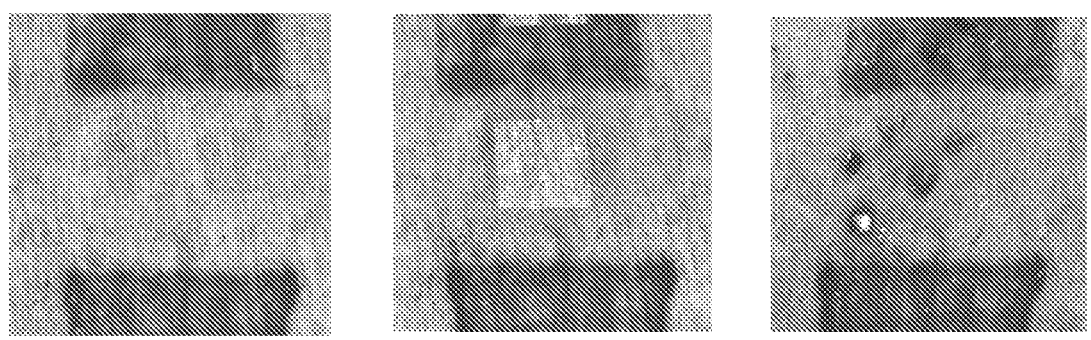
FIG. 8B illustrates images of a native skin test site at various stages of treatment.

FIG. 8B shows a set of images of a pig skin test site that was scanned using a laser beam having a scan rate of 200 mm/s along a scan line, a repetition rate of 20 kHz, a wavelength of about 1060 nm, a pulse duration of about 100 nanoseconds, and an output power of 8 W. The distance between adjacent scan lines was about 25 μm. The focal region of the laser beam was located approximately at the surface of the native skin. Image 810 shows the test site just before treatment, image 812 shows the test site immediately after treatment, and image 814 shows the test site 24 hours after treatment. Several biopsy samples of the treated skin tissue that were taken can be seen in image 814. Under these irradiation conditions, plasma formation was observed in the pig skin due to irradiation of the laser beam.

Example 6

Figure 8C:
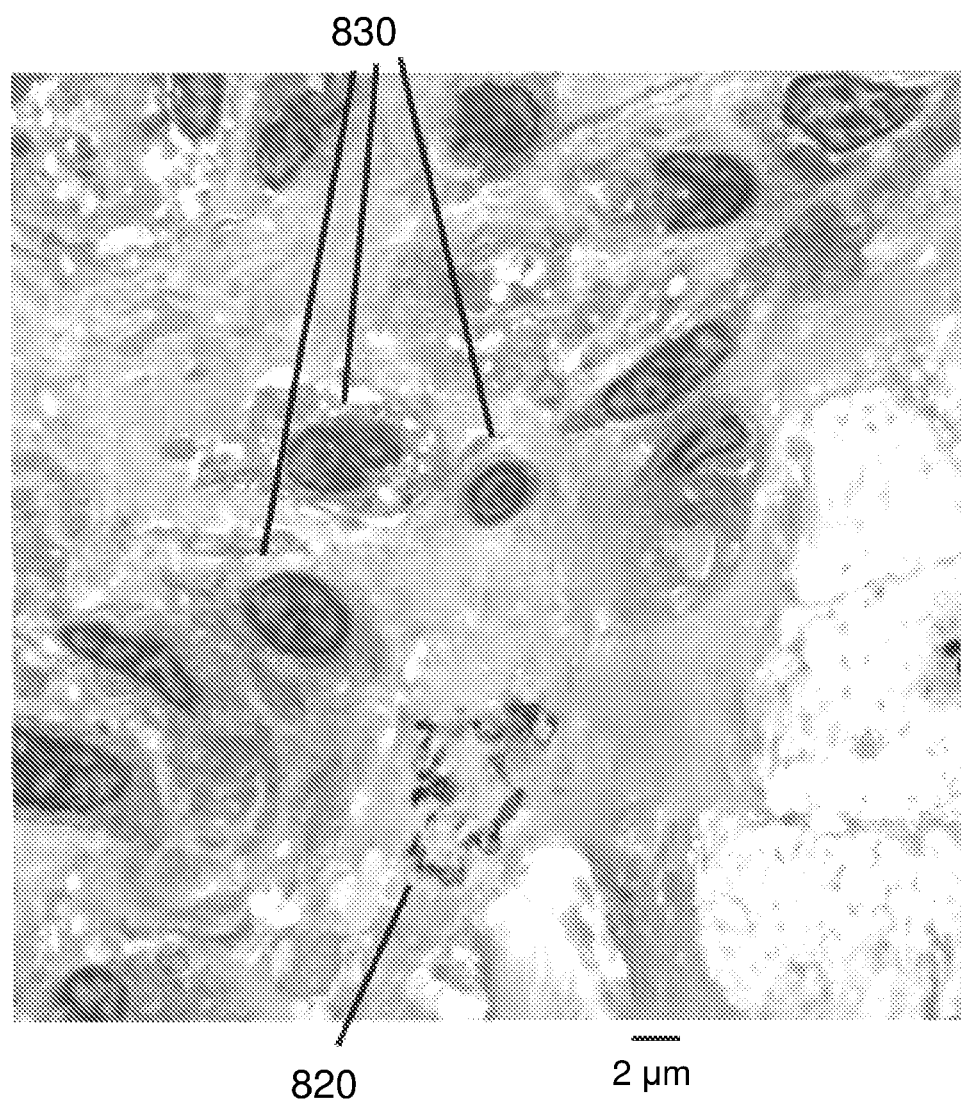
FIG. 8C is an exemplary image of a biopsy taken from the native skin test site shown in FIG. 8B taken by an electron microscope (EM)

FIG. 8C illustrates an exemplary image of a biopsy taken from the native skin test site taken by an electron microscope (EM) described in Example 5 and shown in FIG. 8B. An obliterated cell 820 and unaltered cells 830 can be observed. The obliterated cell 820 contains melanin and the obliteration is believed to have resulted from treatment by the laser beam. The unaltered cells 830 are located as close as about 5 microns to the obliterated cell 820. The unaltered cells 830 contain generally no melanin, and are believed to have remained vital after treatment.

Example 7

Figure 9:
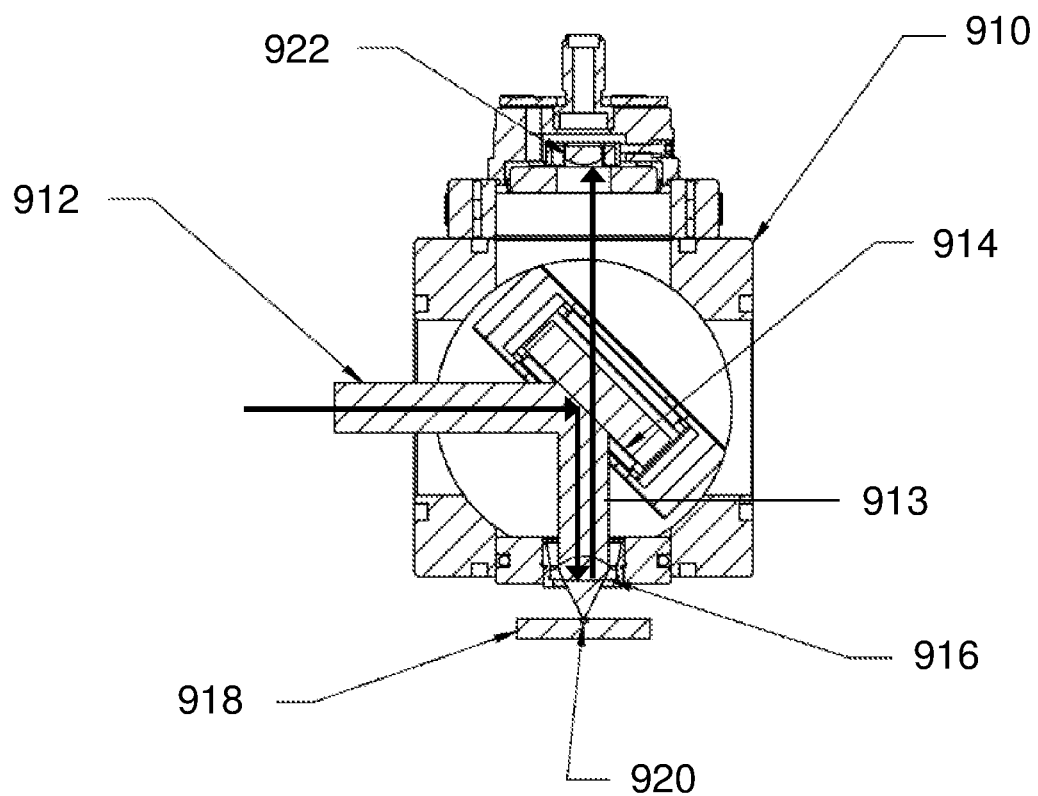
FIG. 9 is a side cross-sectional view of an exemplary system for in vivo plasma detection in a tissue.

FIG. 9 shows a cross-sectional view of a system 910 for generating and detecting plasma formation in vivo in a tissue sample (e.g., human skin, sow skin, and the like) according to an exemplary embodiment of the present disclosure that was used in Examples 8-10 described herein. The exemplary system 910 includes an optical element 914 that receives a collimated laser beam 912 and directs the collimated laser beam towards a focusing arrangement 916 (e.g., a lens). The focusing arrangement 916 focuses the laser beam 912 to a focal region 920 which is located in the tissue sample 918. The focused laser beam generates thermionic plasma at the focal region 920 using thermionic plasma initiation. The thermionic plasma generates a further radiation 913. The optical element 914 receives the plasma-generated radiation 913, and transmits it towards a spectrometer. A fiber coupler 922 receives the radiation 913 and directs it to a spectrometer via a fiber optic.

The optical element 914 can be selected based on the spectral composition of the laser beam 912 and emitted radiation 913. For example, exemplary properties of the optical element 914 can be selected to substantially reflect spectral components of the laser beam 912, and substantially transmit spectral components of the emitted radiation 913. In one exemplary embodiment, the laser beam 912 can include 1060 nm wavelength. The corresponding optical element 914 that was used is a Thorlabs NB1-K14 Nd:YAG Mirror that reflects wavelengths ranging from about 1047 nm to about 1064 nm. The reflected portion of the laser beam 912 is imaged and focused by focusing arrangement 916. The used in this exemplary apparatus 900 includes a Thorlabs C240TME-C mounted diffraction-limited aspheric lens, which has a focal length of 8 mm and a numerical aperture (NA) of about 0.5. The laser beam 912 is focused to a focal region 920 that can be located in the tissue 918, based on the distance between the focusing arrangement 916 and the tissue 918. Thermionic plasma can be generated in portions of the focal region that include a target chromophore (e.g., melanin tattoo, carbon tattoo, clear acrylic plastic sample, tinted acrylic plastic sample, and the like).

Radiation 913 emitted from the plasma generated in the tissue 918 at the focal region 920 can be imaged by the focusing arrangement 916, and transmitted by the optical element 914 to impinge on a first end of a fiber optic (not shown) by a fiber coupler 922. The fiber coupler used in apparatus 900 is a Thorlabs PAF-SMA-7-A fiber collimator and coupler. A second end of the fiber optic is coupled to an Ocean Optics HR2000+ ES spectrometer. A notch filter (not shown) is included between the optical element 914 and the fiber coupler 922 to block/dissipate spectral components of the emitted radiation 913 that have wavelengths substantially similar to the spectral component of the laser beam 912.

The tissue sample 918 can be mounted on a motorized stage that can be moved independently along the x, y, and z axes. By such exemplary movement, the motorized stage can place a particular portion of the tissue sample 918 into the focal region 920 of the focused laser beam 912. For example, a working distance between the tissue sample 918 and the focus optic 916 can be varied (e.g., along the z-axis) to control a depth of the focal region 920 of the laser beam 912 within the tissue sample 918. The motorized stage also moves in the x-y plane and can move certain portions of the tissue sample 918 (e.g., a portion that includes a target chromophore) into the focal region 920.

Figure 10A:
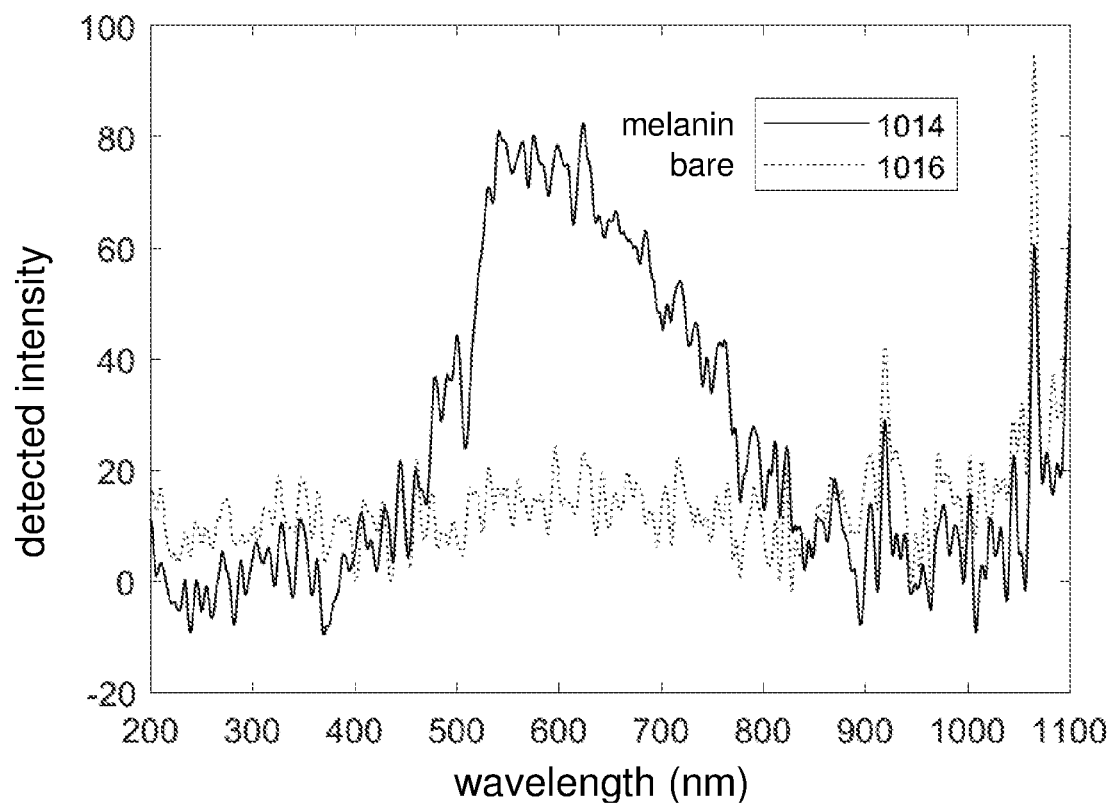
FIG. 10A is a plot of detected intensity spectra for irradiated tissue containing a melanin tattoo and tissue not tattooed with melanin.

FIG. 10A illustrates an exemplary plot of the intensity spectrum detected by the spectrometer of the system 900 described above. In this example, the tissue sample 918 that includes a melanin tattoo is placed on the motorized stage beneath the focus optic 916. The focal region 920 is provide about 0.2 mm below the surface of the tissue sample 918. The melanin tattoo is located approximately between a quarter of a millimeter and a millimeter below the dermis of the skin sample.

The horizontal axis provided in FIG. 10A represents wavelength (in nanometers) of the detected radiation. The vertical axis represents intensity of the detected radiation at each wavelength. Two spectra are displayed in FIG. 10A, i.e., a melanin tattoo spectrum 1014, and a bare skin spectrum 1016. The melanin tattoo spectrum 1014 represents a measurement taken during irradiation of the tissue sample at the location of the melanin tattoo. The bare skin spectrum 1016 represents a measurement taken during irradiation of the sample away from the location of the melanin tattoo. The melanin tattoo spectrum 1014 shows a presence of a broad-spectrum light during irradiation centered at about 600 nm and covering the visible spectrum. In contrast, the bare skin spectrum 1016 has relatively lower intensities for visible light (e.g., for wavelengths ranging from about 500 nm to about 800 nm).

The operating parameters of the exemplary system 900 for detection of the intensity plot in FIG. 10A can be as follows. For example, the laser beam 912 has a repetition rate of 20 KHz, and includes laser pulses having a time duration of about 100 nanoseconds and pulse energy of about 0.5 mJ per pulse. The treatment site is treated with a scan rate (e.g., x-y or lateral speed of the laser beam 912 over the test site) of about 100 mm/s along multiple scan lines. The spectrometer was adjusted to capture light over a 5000 millisecond period, and was triggered when an irradiation impinges on the spectrometer.

Figure 10B:
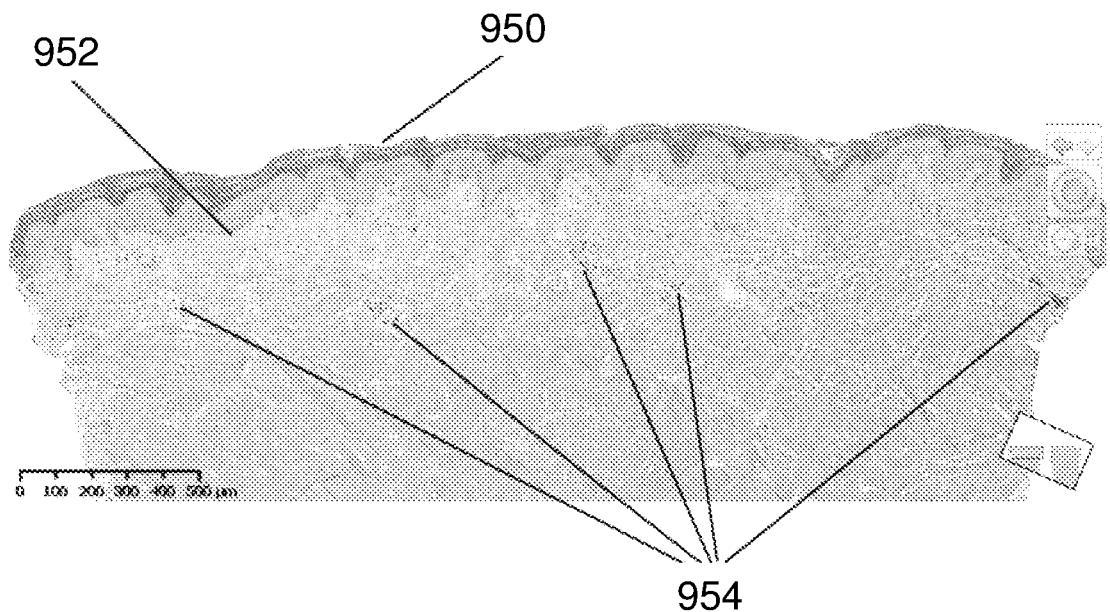
FIG. 10B is a photomicrograph image of a section of the tissue sample containing melanin tattoo that was irradiated to obtain an intensity spectrum in FIG. 10A.

FIG. 10B shows a photomicrograph image of a section of the tissue sample containing melanin tattoo that was irradiated to obtain the intensity spectrum 1014 in FIG. 10A. Tissue surface 950 is shown at the top of the image of FIG. 10B. An epidermis-dermis junction 952 demarcates the epidermis and dermis layers of the skin. Melanin globules 954 present in the dermis constitute the melanin tattoo.

Example 8

Figure 11:
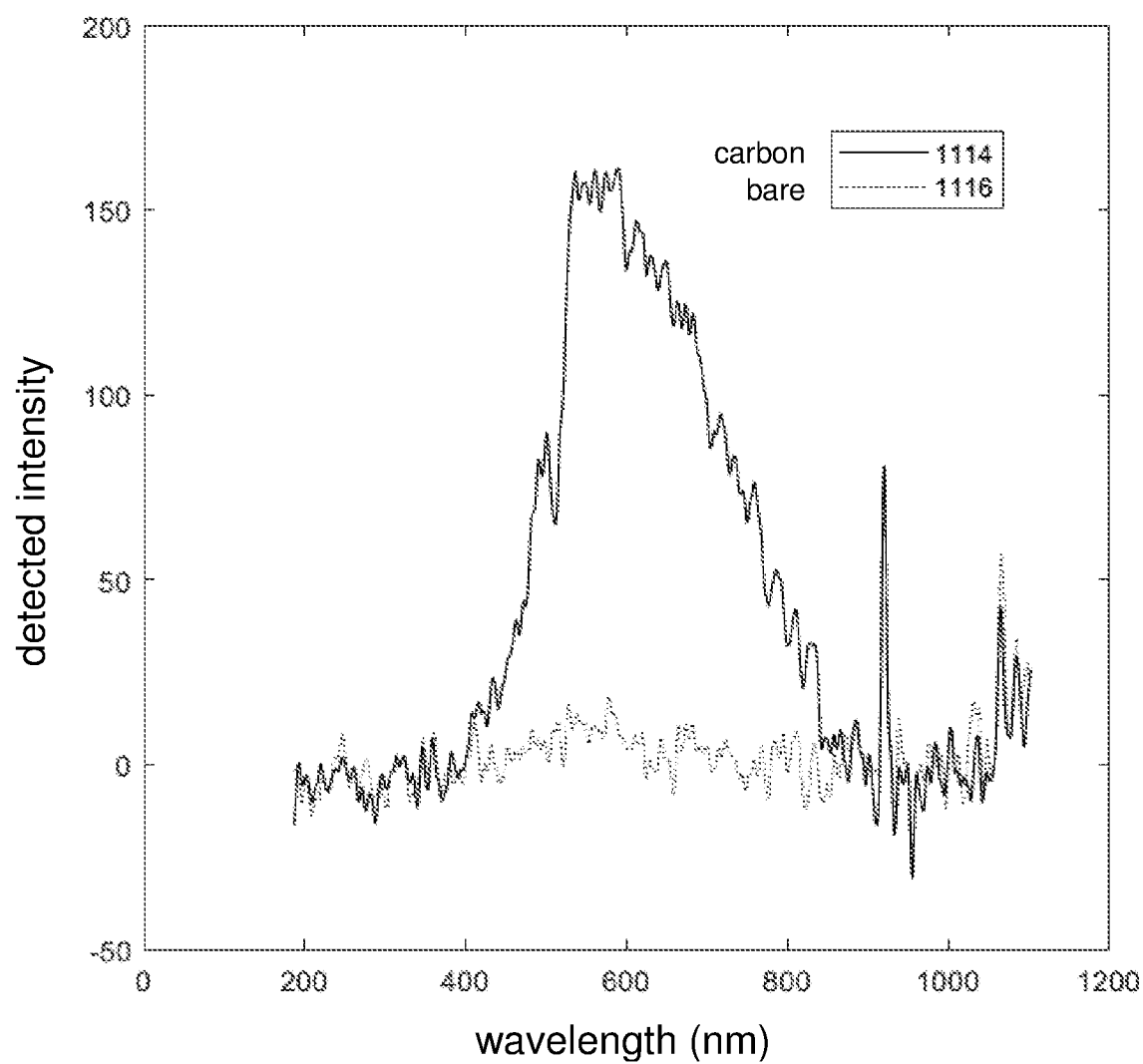
FIG. 11 is a plot of detected intensity spectra for irradiated tissue containing a carbon tattoo and tissue not tattooed with carbon.

FIG. 11 illustrates an exemplary plot of further intensity spectra detected by the spectrometer of the system 900 described in Example 7. In this example, the tissue sample 918 included a carbon tattoo and was placed on the motorized stage beneath the focusing arrangement 916. The focal region 920 was located about 0.2 mm below the surface of the tissue sample 918. The carbon tattoo was located between approximately a quarter of a millimeter and a millimeter below the dermis of the skin sample.

The horizontal axis provided in FIG. 11 represents wavelength (in nanometers) of the detected radiation. The vertical axis represents intensity of the detected radiation at each corresponding wavelength. Two spectra are displayed in FIG. 11: a spectrum 1114 obtained during irradiation of a sample region containing a carbon tattoo, and a spectrum 1116 obtained during irradiation of a sample region that did not have any carbon tattoo present. The carbon tattoo spectrum 1114 shows a presence of a broad-spectrum of emitted light during irradiation centered at about 600 nm and covering the visible spectrum. The bare skin spectrum 1116 has relatively lower intensities for visible light (e.g., for wavelengths ranging from about 400 nm to about 800 nm).

The operating parameters of the system 900 for detection of the intensity plot shown in FIG. 11 are as follows. The laser beam 912 has a repetition rate of about 20 KHz, and includes laser pulses having a time duration of about 100 nanoseconds and pulse energy of about 0.5 mJ per pulse. The treatment site was treated with a scan rate (e.g., lateral or x-y speed of the laser beam 912 along the test site) of about 100 mm/s along multiple scan lines. The spectrometer was adjusted to capture light over a 5000 millisecond period, and was triggered when an irradiation impinges on the spectrometer.

Example 9

Figure 12:
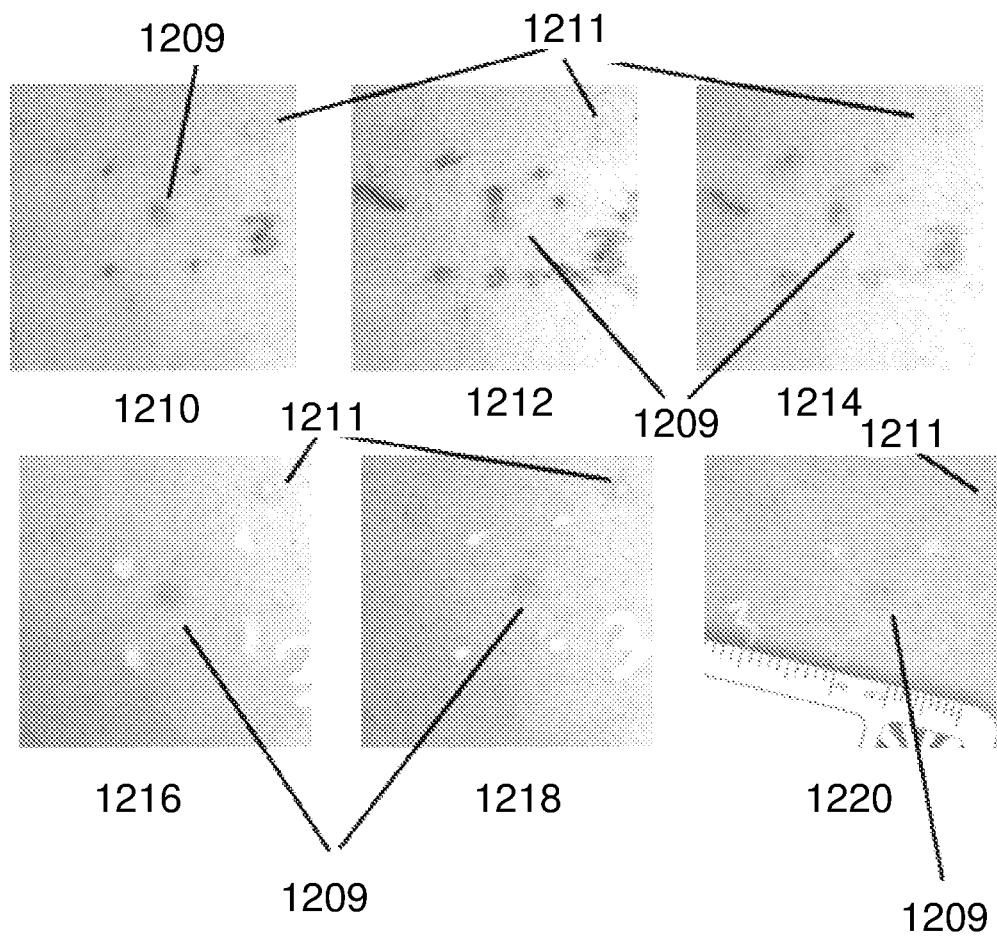
FIG. 12 illustrates images of an exemplary test site at various stages of treatment.

FIG. 12 illustrates exemplary images of an exemplary test site at various stages of treatment using the treatment system 900 described in Example 7. Image 1210 illustrates the test site prior to the treatment that includes a region 1209 for treatment and a second control region 1211. In these images, the region to be treated (e.g., region 1209 having hyperpigmentation resulting from post-acne scarring) is generally placed in the center of the test site. The control region 1211 is left untreated and is located in the top right corner of the test site.

The treatment region 1209 was scanned using system 900 with a laser beam having an output power of 10 W, a wavelength of about 1060 nm, a pulse duration of about 100 nanoseconds and a repetition rate of 20 kHz. The treatment region 1209 was treated with a scan rate (e.g., lateral speed of the laser beam along the test site) of about 100 mm/s along multiple scan lines. The distance between the scan lines was about 25 μm. Additionally, six layers of the test site having varying depths (e.g., 300, 350, 400, 450, 500, and 550 μm from the surface of the test site) were scanned.

Images 1212-1220 illustrate the overall treatment site at various times after treatment. Image 1212 shows the test site immediately after treatment. Image 1214 shows the test site 24 hours after treatment. Images 1216, 1218, and 1220 show the test site at 1 week, 1 month, and 3 months after treatment, respectively. Observation of images 1212-1220 suggests that the color of the treatment region 1209 gradually fades with the passage of time. Additionally, the color of the control region 1211 does not appear to fade as compared to the treatment region 1209 during the same period. Further, a surface texture of the treatment region 1209 appears to smoothen after treatment. The surface texture of the treatment region 1209 appears generally as smooth as the surrounding skin 3 months after treatment (image 1220). However, a surface texture of the control region 1211 remains generally unchanged in images taken after treatment. As evidenced by the images of FIG. 12, the treatment site does not appear to be adversely affected (e.g., due to injuries) by the treatment. Treatments using average laser beam power outputs of up to 20 W (together with other parameter ranges described herein) appear to be safe and not generate unwanted damage in the skin tissue.

Example 10

Figure 13:
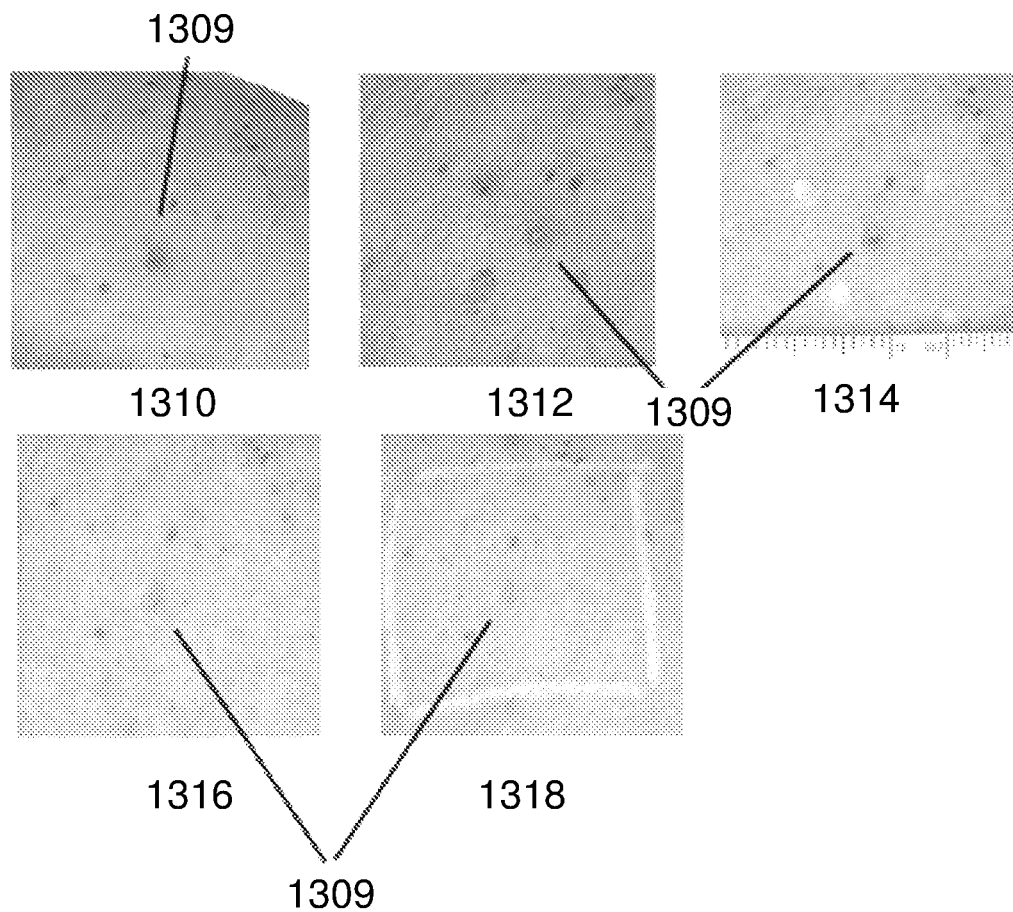
FIG. 13 illustrates images of another exemplary test site at various stages of another treatment.

FIG. 13 shows exemplary images of an exemplary test site at various stages of treatment by the treatment system 900 described in Example 7. Image 1310 illustrates the test site prior to the treatment that includes a region 1309. The region to be treated (e.g., region 1309 having hyperpigmentation resulting from post-acne scarring) is generally placed in the center of test site. The test site was irradiated using the following parameters. The laser beam had an output power of 20 W, a wavelength of about 1060 nm, a pulse duration of about 100 nanoseconds and a repetition rate of 20 kHz. The treatment site was treated with a scan rate (e.g., lateral speed of the laser beam over the test site) of about 100 mm/s along multiple scan lines. The distance between the scan lines was about 25 μm. Additionally the test site was scanned successively at 8 different depths (e.g., 200, 250, 300, 350, 400, 450, 500, and 550 μm from the surface of the test site).

Images 1312-1318 show the treatment site at various times after treatment. Image 1312 shows the test site immediately after treatment. Images 1314, 1316, and 1318 show the test site 24 hours, 1 week, and 1 month after the irradiation treatment, respectively. Images 1312-1318 suggest that the color of the treatment region 1309 gradually fades with the passage of time. Additionally, a surface texture of the treatment region 1309 appears to smoothen after treatment. The surface texture of the treatment region 1309 is generally as smooth as the surrounding skin 1 month after treatment. Although some redness was observed immediately post-treatment in image 1312, the redness was not present in the 24-hour image 1314.

The exemplary parameters and calculations described in the Examples herein and in other parts of the present disclosure can be used to determine other parameter combinations that can also generate selective plasma formation at chromophore sites, using conventional geometric and energy relationships. For example, the amount of energy delivered to each location in the tissue can be reduced by half by doubling the scan speed or by reducing the average laser power output by half. However, the faster scan speed reduces the local dwell (exposure) time in half, whereas reducing the average laser output power leaves the dwell time unaffected. Doubling the spot size/diameter (with all other laser parameters kept fixed) will reduce the local power and energy densities by a factor of 4. Such larger spot sizes (at a fixed scan speed) will also double the local dwell time at a location in the tissue, because the wider spot will take twice as long to pass through a particular point in the tissue.

Accordingly, further combinations of pulse durations, power output, pulse frequency, scan rate, focal spot sizes, etc. that lead to selective plasma formation can be readily estimated when one or more parameters are varied within the exemplary sets of values presented herein. Parameters that should remain close to those presented here to achieve similar effects in tissue include local power and energy densities, and local dwell times. Further variation of such parameters to account for changes in other factors such as different wavelengths or other chromophores can also be estimated, e.g., by accounting for the changes in energy absorption efficiency by the chromophore, etc.

Further, although the examples herein are described primarily with respect to selective plasma formation at chromophore sites in biological tissues such as skin, similar principles can be applied to selectively generate plasmas in other irradiated tissues (e.g. brain tissue, etc.) and in other materials, e.g. non-biological materials that have relatively weak absorption coefficients and contain regions of highly-absorbing chromophores.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

What is claimed is:

1. A method, comprising:
   emitting, by a laser system including at least one laser, at least one laser beam having a nanosecond pulse duration;
   focusing, by an optical system including at least one lens, the at least one laser beam to a focal region at a selected distance from a surface of a tissue including pigmented and unpigmented regions; and
   controlling, using a control arrangement, the laser system and the optical system to cause an irradiation energy transferred to the focal region of the at least one laser beam at a wavelength that is selectively absorbed by the pigmented region of the tissue,
   wherein the at least one laser beam generates a plasma locally at the pigmented regions of the tissue when the focal region overlaps with the pigmented regions, thereby causing damage to the pigmented regions of the tissue within the focal region, and
   wherein the at least one laser beam avoids damage at the unpigmented regions of the tissue when the focal region does not overlap with the pigmented region and overlaps with the unpigmented region.

2. The method of claim 1, wherein the plasma is a thermionic plasma, and wherein the generation of the thermionic plasma (i) causes damage to the pigmented regions of the tissue within the focal region when the focal region overlaps with the pigmented regions, and (ii) avoids a generation of the thermionic plasma at the unpigmented regions of the tissue and avoids damage at the unpigmented regions of the tissue when the focal region does not overlap with the pigmented region and overlaps with the unpigmented region.

3. The method of claim 1, wherein a numerical aperture of the at least one lens is between 0.5 and 0.9.

4. The method of claim 1, wherein the at least one laser beam has a wavelength in the range of about 600 nm to about 1100 nm when measured in air.

5. The method of claim 1, wherein a peak intensity of the at least one laser beam is at least about $10^8$ W/cm$^2$ in the focal region.

6. The method of claim 1, wherein the focal region is located within the dermis.

7. The method of claim 1, wherein the at least one laser beam comprises (i) a first laser pulse configured to generate a thermionic emission of electrons, and (ii) a second laser pulse configured to generate the plasma that is a thermionic plasma.

8. The method of claim 1, wherein a spot size of the focal region is in the range of about 5 μm to about 100 μm when measured in air.

9. The method of claim 1, wherein the at least one lens is configured to vary the selected distance of the focal region with respect to the surface of the tissue.

10. The method of claim 9, wherein the selected distance of the focal region from the surface of the tissue is in the range of about 5 μm to about 1000 μm.

11. The method of claim 1, wherein the at least one lens comprises a plurality of micro-lenses.

12. The method of claim 11, further comprising directing a single laser beam over at least one portion of the plurality of micro-lenses to produce a plurality of focal regions simultaneously.

13. The method of claim 11, further comprising directing a single laser beam over at least a portion of the plurality of micro-lenses to produce a plurality of focal regions non-simultaneously.

14. The method of claim 11, further comprising:
   emitting a plurality of laser beams; and
   directing at least one of the plurality of laser beams on one or more of the plurality of micro-lenses.

15. The method of claim 1, wherein the pigmented regions of the tissue comprise a chromophore.

16. The method of claim 15, wherein the chromophore comprises at least one of melanin, tattoo inks, hemoglobin, sebaceous glands, subcutaneous fat, hair bulb, lipids in cell membrane, fat surrounding organs, vessels, or drug components.

17. The method of claim 1, further comprising detecting, by one or more sensors, one or more of a velocity or a position of an apparatus, that includes the laser system and the optical system, relative to the surface of the tissue.

18. The method of claim 17, further comprising:
   receiving, by a feedback control configuration, data characterizing the one or more of the velocity or the position detected by the one or more sensors; and
   controlling, by the feedback control configuration, at least one of a pulse duration, a pulse frequency or a pulse energy of the at least one laser beam.

19. The method of claim 1, further comprising controlling, by the laser system, a time interval between temporally adjacent laser pulses of the at least one laser beam such that a travel time for a movement of the focal region from a first location in the tissue to a second location in the tissue is less than the time interval.

20. The method of claim 19, wherein the time interval between the temporally adjacent laser pulses is less than 50 milliseconds.

21. A method, comprising:
   emitting, by a laser system that includes at least one q-switched laser, at least one laser beam;

focusing, by an optical system that includes at least one lens, the at least one laser beam to a focal region at a selected distance from a surface of a tissue that includes pigmented and unpigmented regions; and controlling, using a control arrangement, the laser system and the optical system to cause an irradiation energy transferred to the focal region of the at least one laser beam at a wavelength that is selectively absorbed by the pigmented region of the tissue, wherein, when the focal region overlaps with the pigmented regions, the at least one laser beam generates a thermionic plasma locally at the pigmented regions of the tissue, thereby causing damage to the pigmented region of the tissue within the focal region, and wherein, when the focal region does not overlap with the pigmented regions and overlaps with the unpigmented region, the at least one laser beam avoids generation of the thermionic plasma damage at the unpigmented regions and avoids damage at the unpigmented regions of the tissue.

22. The method of claim 21, wherein a numerical aperture of the at least one lens is between 0.5 and 0.9.

23. The method of claim 21, wherein the at least one laser beam has a wavelength in the range of about 600 nm to about 1100 nm when measured in air.

* * * * *